US 6,534,650 B2

(12) United States Patent
Klimkowski et al.

(10) Patent No.: US 6,534,650 B2
(45) Date of Patent: Mar. 18, 2003

(54) BENZISOXAZOLE AND 4-AMIDINO-3-HYDROXYPHENYL CHEMICAL INTERMEDIATES

(75) Inventors: Valentine J Klimkowski, Carmel; Aaron L Schacht, Plainfield; Michael R Wiley, Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/803,345

(22) Filed: Mar. 9, 2001

(65) Prior Publication Data

US 2001/0018423 A1 Aug. 30, 2001

Related U.S. Application Data

(62) Division of application No. 09/202,626, filed as application No. PCT/US97/10745 on Jun. 20, 1997, now Pat. No. 6,200,967.
(60) Provisional application No. 60/020,371, filed on Jun. 25, 1996.

(51) Int. Cl.$^7$ .................. C07D 205/06; C07D 205/05; C07D 209/52; C07D 413/12; C07D 413/14
(52) U.S. Cl. .................. 540/461; 540/580; 540/593; 540/594; 546/192; 546/198; 546/113; 546/146; 546/147; 548/241; 548/571; 548/572; 548/452; 548/453; 548/950; 564/247
(58) Field of Search .................. 540/461, 580, 540/593, 594; 546/113, 146, 147, 192, 198; 548/241, 452, 453, 571, 572, 950; 564/247

(56) References Cited

U.S. PATENT DOCUMENTS

| 596,797 A | 1/1898 | Tauber |
| 3,189,649 A | 6/1965 | Rosiger .................. 260/564 |
| 3,632,593 A | 1/1972 | Gautier .................. 260/296 |
| 4,244,865 A | 1/1981 | Ali .................. 260/112.5 |
| 4,322,429 A | 3/1982 | Burow .................. 424/272 |
| 4,336,264 A | 6/1982 | Wickiser .................. 424/272 |
| 4,346,078 A | 8/1982 | Bajusz et al. .................. 424/177 |
| 4,571,255 A | 2/1986 | Nielsen .................. 71/88 |
| 4,661,522 A | 4/1987 | Beetz .................. 514/632 |
| 5,385,927 A | 1/1995 | Michel et al. .................. 514/397 |
| 5,455,348 A | 10/1995 | Austel et al. .................. 544/238 |
| 5,489,583 A | 2/1996 | Mack et al. .................. 514/183 |
| 5,498,779 A | 3/1996 | Neises .................. 514/428 |
| 5,523,278 A | 6/1996 | Wepplo .................. 504/271 |
| 5,561,146 A | 10/1996 | Kim et al. .................. 514/326 |
| 5,583,146 A | 12/1996 | Kimball et al. .................. 514/326 |
| 5,602,253 A | 2/1997 | Antonsson et al. .................. 544/330 |
| 5,618,843 A | 4/1997 | Fisher et al. .................. 514/567 |
| 5,629,321 A | 5/1997 | Okumura et al. .................. 514/307 |
| 5,705,487 A | 1/1998 | Schacht et al. .................. 514/19 |
| 5,756,754 A | 5/1998 | O'Malley et al. .................. 548/241 |
| 5,856,503 A | 1/1999 | Aebi et al. .................. 548/207 |
| 5,863,929 A | 1/1999 | Klimkowski et al. |
| 6,008,367 A | 12/1999 | Klimkowski et al. |
| 6,034,104 A | 3/2000 | Klimkowski et al. |
| 6,160,176 A | 12/2000 | Klimkowski et al. |
| 6,200,967 B1 | 3/2001 | Klimkowski et al. |

FOREIGN PATENT DOCUMENTS

| DE | 151447 B | 10/1981 |
| EP | 601 459 | 6/1994 |
| EP | 623 595 | 11/1994 |
| EP | 623 596 | 11/1994 |
| EP | 648 780 | 4/1995 |
| EP | 669 317 | 8/1995 |
| EP | 686 642 | 12/1995 |
| JP | 08020597 | 1/1996 |
| WO | WO 93/11152 | 6/1993 |
| WO | WO 94/29336 | 12/1994 |
| WO | WO 95/23609 | 9/1995 |
| WO | WO 95/35309 | 12/1995 |
| WO | WO 96/17860 | 6/1996 |
| WO | WO 96/24609 | 8/1996 |
| WO | wo 96/25426 A1 * | 8/1996 |
| WO | WO 96/25426 | 8/1996 |
| WO | WO 97/02284 | 1/1997 |

OTHER PUBLICATIONS

U.S. patent application Ser. No. 09/614,179, Jul. 2000, Klimkowski et al.

Geratz, J. D., "Inhibition of Thrombin, Plasmin, and Plasminogen Activation by Amidino Compounds," *Thromb. Diath. Haemorrh.*, 23, 486–499 (1970).

Asghar, S. S., et al., "Inhibition of Cir, Cis and Generation of Cis by Amidino Compounds," *Biochimica et Biophysica Acta,* 317, 539–548, (1973).

(List continued on next page.)

Primary Examiner—Mukund J. Shah
Assistant Examiner—Thomas McKenzie
(74) Attorney, Agent, or Firm—Thomas E. Jackson

(57) ABSTRACT

This invention relates to compounds of Formula V $$H—Y—G—R \qquad V$$

and Formula VI

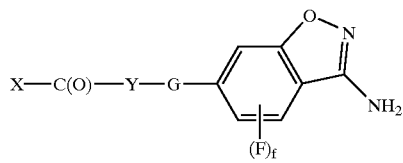

(wherein f, X, Y, G and R have the values defined in the description) which are useful as intermediates for the preparation of compounds, or pharmaceutically acceptable salts thereof, which are useful as thrombin inhibitors, coagulation inhibitors and agents for the treatment of thromboembolic disorders.

17 Claims, No Drawings

OTHER PUBLICATIONS

Asghar, S. S., et al., "Human Plasma Kallikreins and Their Inhibition by Amidino Compounds," *Biochimica et Biophysica Acta,* 438, 250–264, (1976).

Bajusz, S., "Interaction of Trypsin–like Enzymes with Small Inhibitors," *Symposia Biologica Hungarica,* 25, 277–298, (1984).

Shutske, G. M., et al., "A Novel Synthesis of 3–Amino–1, 2–Benzisoxazoles— an Entry into Isoxazolo[3,4,5–ef] [1,4] benzoxazepine Ring System," *J. Heterocyclic chem.,* 26, 1293–1298, (1989).

Reguera, R. et al., "Putrescine Uptake Inhibition by Aromatic Diamidines in *Leishmania infantum* Promastigotes", *Biochem. Pharm.,* 47, 1859–1866, (1994).

Misra, Raj N., et al., "Argatroban Analogs: Synthesis Thrombin Inhibitory Activity and Cell Permeability of Aminoheterocyclic Guanidine Surrogates," *Bioorg. & Med. Chem. Letters,* 4, 2165–2170, (1994).

Scarborough, R. M., "Anticoagulant Strategies Targeting Thrombin and Factor Xa," *Annual Reports in Medical Chemistry,* 30, 71–80, (1995).

Edmunds, J. J. et al., "Thrombin and Factor Xa Inhibition, "*Annual Reports in Medical Chemistry,* 31, 51–60, (1996).

Hilpert, K., et al., "Design and Synthesis of Potent and Highly Selective Thrombin Inhibitors," *J. Med. Chem.,* 37, 3889–3901, (1994).

Handin et al., Bleeding and Thrombosis, Harrison's Principles of Internal Medicine, Thirteenth Edition, pp. 317–322, 1994.

Silverman, Structure Modifications to increase Potency and Therapeutic Index, The Organic Chemistry of Drug, Design and Drug Action, pp. 15–22, 1992.

* cited by examiner

BENZISOXAZOLE AND 4-AMIDINO-3-HYDROXYPHENYL CHEMICAL INTERMEDIATES

This application claims the benefit of U.S. Provisional Application No. 60/020,371, filed Jun. 25, 1996, and is a divisional of copending application Ser. No. 09/202,626, U.S. Pat. No. 6,200,967, granted Mar. 13, 2001, which is the U.S. national stage application of International Application No. PCT/US97/10745, filed on Jun. 20, 1997, the entire disclosure of which herein is incorporated by reference.

This invention relates to thrombin inhibitors which are useful anticoagulants in mammals. In particular it relates to ortho-hydroxybenzamidine derivatives having high anticoagulant activity,. Thus, this invention relates to new inhibitors of thrombin, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation.

Anticoagulation is currently achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because surface-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin. See, for example Robert M. Scarborough, *Annual Reports in Medicinal Chemistry*, (1995), 30, 71–80, where inhibitors which lack a polarizable functionality to interact with the active site Ser-195 hydroxy group of thrombin are termed active site inhibitors. Active site inhibitors in which the C-terminal moiety comprises an unsubstituted or certain substituted amidinophenyl (benzamidine) moiety are exemplified in EP 623596, WO 94/29336, WO 95/23609 and WO 95/35309. The amidinophenyl moiety is strongly basic, a property which militates against good oral bioavailability. See, for example R. J. Misra, et al., *Bioorganic & Medicinal Chemistry Letters*, (1994), 4, 2165–2170, where less basic argatroban analogs were shown to retain useful thrombin inhibitory potency while exhibiting better distribution properties as shown by enhanced Caco-2 cell permeability. As discussed below, the compounds disclosed herein retain useful thrombin inhibitory potency while exhibiting improved distribution coefficients as a result of their particularly substituted amidinophenyl moieties. Subsequent to the priority date for the instant application, there were published international patent applications WO 96/24609 and WO 96/25426 disclosing certain substituted amidinophenyl compounds, including D-cyclohexylglycyl-N-[[4-(aminoimino-methyl)-3-hydroxyphenyl]methyl-L-prolinamide dihydrochloride at Example 53 of WO 96/25426.

Although the heparins and coumarins are effective anticoagulants, no generally accepted commercial drug has yet emerged from the small synthetic molecules; and despite the continuing promise for this class of compounds, there still exists a need for anticoagulants which act selectively on thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent thrombin inhibitors that may have high bioavailability following oral administration.

According to the invention there is provided a compound having the Formula I $$X-C(O)-Y-G-R \qquad\qquad I$$

wherein

X—C(O)— is D-prolinyl, D-homoprolinyl, $R^m$—$(CH_2)_g$—NH—$CH_2$—C(O)—,

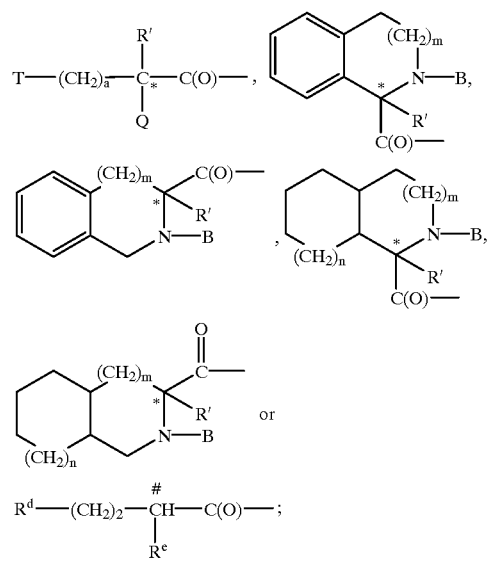

in which $R^d$ is carboxy or methylsulfonyl;

$R^e$ is $NHR^c$, $NHCOR^c$ or $NHCOOR^c$; in which $R^c$ is $(C_1$–$C_6)$alkyl, $(C_3$–$C_8)$cycloalkyl or a $(C_3$–$C_8)$cycloalkyl-$(C_1$–$C_6)$alkyl radical of 4–10 carbons;

T is $(C_3-C_8)$cycloalkyl, $(C_1-C_8)$alkyl,

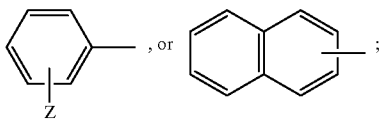

a is 0, 1 or 2; and

Q is —OH, $(C_1-C_4)$alkoxy, or —NH—A;

A is hydrogen, $(C_1-C_4)$alkyl, R"$SO_2$—, R"OC(O)—, R"C(O)—, R"C(O)— or —$(CH_2)_g$—$R^m$;

g is 1, 2, or 3;

B is hydrogen or $(C_1-C_4)$alkyl;

R' is hydrogen or $(C_1-C_4)$alkyl;

R" is $(C_1-C_4)$alkyl, $(C_1-C_4)$fluoroalkyl bearing one to five fluoros, —$(CH_2)_d$—$R^m$, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^m$ is —COO$R^b$, —$SO_2$($C_1-C_4$ alkyl), —$SO_3$H, —P(O)(O$R^b$)$_2$ or tetrazol-5-yl;

$R^n$ is —COO$R^b$ or tetrazol-5-yl;

each $R^b$ is independently hydrogen or $(C_1-C_4)$alkyl;

d is 1, 2, or 3;

n is 0, 1, or 2;

n is 0, 1, or 2; and

Z is hydrogen, $(C_1-C_4)$alkyl, $(C_1-C_4)$alkoxy, hydroxy, halo or $(C_1-C_4)$alkylsulfonylamino;

—Y—G— is

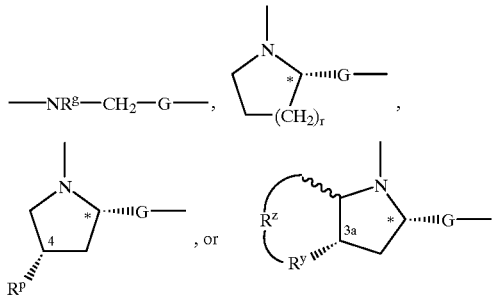

in which r is 0, 1 or 2;

$R^g$ is $(C_1-C_6)$alkyl, $(C_3-C_8)$cycloalkyl, or —$(CH_2)_p$—L—$(CH_2)_q$—T';

$R^p$ is $(C_1-C_6)$alkyl, $(C_3-C_8)$cycloalkyl, or —$(CH_2)_p$—L—$(CH_2)_q$—T';

where p is 0, 1, 2, 3, or 4; L is a bond, —O—, —S—, or —NH—; q is 0, 1, 2 or 3; and T' is $(C_1-C_4)$alkyl, $(C_3-C_8)$cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

$R^y$ is —$CH_2$—, —O—, —S—, or —NH—; and $R^z$ is a bond or, when taken with $R^y$ and the three adjoining carbon atoms, forms a saturated carbocyclic ring of 5–8 atoms, one atom of which may be —O—, —S—, or —NH—;

—G—R is —C(O)—NH—$(CH_2)_s$—R, —$CH_2$—NH—$(CH_2)_s$—R, —$CH_2$—NH—C(O)—R or —$(CH_2)_t$—O—R in which s is 1 or 2 and t is 1, 2 or 3; and R is a 4-amidino-3-hydroxyphenyl group bearing 0, 1, 2 or 3 fluoro substituents;

or a pharmaceutically acceptable salt thereof.

In addition to a compound of Formula I, the present invention provides a pharmaceutical composition comprising a compound of Formula I, or a pharmaceutically acceptable salt thereof, in association with a pharmaceutically acceptable carrier, diluent or excipient.

The present invention further provides a method of inhibiting thrombin comprising administering to a mammal in need of treatment, a thrombin inhibiting dose of a compound of Formula I.

The present invention also provides a method of inhibiting thrombosis in a mammal comprising administering to a mammal in need of treatment, an antithrombotic dose of a compound of Formula I.

This invention relates to new inhibitors of thrombin, pharmaceutical compositions containing the compounds as active ingredients, and the use of the compounds as anticoagulants for prophylaxis and treatment of thromboembolic diseases such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

The term "5- or 6-membered aromatic heterocyclic ring" means any 5- or 6-membered ring that will afford a stable structure containing one or two nitrogen atoms; one sulfur atom; one oxygen atom; one nitrogen and one sulfur atom; or one nitrogen and one oxygen atom. The 5-membered ring has two double bonds and the 6-membered ring has three double bonds.

The term "9- or 10-membered fused bicyclic aromatic heterocyclic group" means any bicyclic group in which any of the above 5- or 6-membered rings is ortho fused to a benzene ring or to a 6-membered heterocyclic aromatic ring as defined above in a manner that will afford a stable structure.

It will be appreciated that many of the above heterocycles may exist in tautomeric forms. All such forms are included within the scope of this invention.

Each of the aromatic or heteroaromatic groups listed for the definition of Ar or R" is independently unsubstituted or substituted with one or two substituents that will afford a stable structure independently selected from halo, hydroxy, $(C_1-C_4)$alkyl, $(C_1-C_4)$alkoxy, amino, mono($C_1-C_4$ alkyl)amino, di($C_1-C_4$ alkyl)amino, -$(CH_2)_j$COOH, mercapto, —S(O)$_h$($C_1-C_4$ alkyl), —NHS(O)$_h$($C_1-C_4$ alkyl), —NHC(O)($C_1-C_4$ alkyl), —S(O)$_h$NH$_2$, —S(O)$_h$NH($C_1-C_4$ alkyl), or —S(O)$_h$N($C_1-C_4$ alkyl)$_2$, h is 0, 1 or 2, and j is 0, 1, 2, 3, or 4.

In the representation of Formula I, the carbonyl functionality of group X—(CO)— is attached to the amine functionality of the —Y— group.

The group

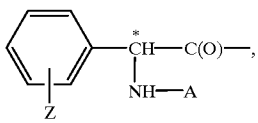

where Z and A are both hydrogen, is referred to at times herein as phenylglycyl and abbreviated Phg. Compounds wherein A is, e.g., methyl, are referred to as the N$^\alpha$-methyl-phenylglycyl group and abbreviated MePhg. Substituted compounds wherein Z is other than hydrogen are referred to by the type and position of the substituent group, e.g., 3'-chlorophenylglycyl or Phg(3-Cl).

The group

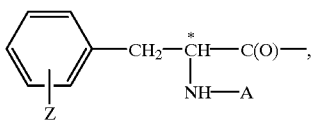

where Z and A are both hydrogen, is referred to at times herein as phenylalanyl and abbreviated Phe. Compounds wherein A is, e.g., methyl, are referred to as the N$^\alpha$-methyl-phenylalanyl group and abbreviated MePhe. Substituted compounds wherein Z is other than hydrogen are referred to by the type and position of the substituent group, e.g., 3'-chlorophenylalanyl or Phe(3-Cl).

The groups

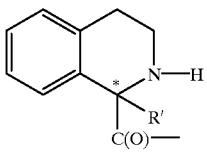 and 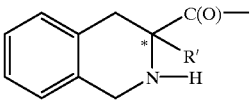

when R' is hydrogen, are referred to at times herein as 1- and 3-tetrahydro-isoquinolinecarbonyl, respectively, and are respectively abbreviated 1-Tiq and 3-Tiq.

The groups

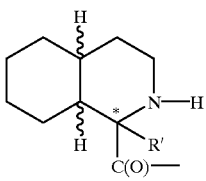 and 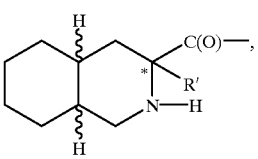

when R' is hydrogen, are referred to at times herein as 1- and 3-perhydro-isoquinolinecarbonyl, respectively, and are respectively abbreviated 1-Piq and 3-Piq. As indicated by the crooked lines, various ring fusion isomers of these substituents exist—this invention contemplates any individual isomer and combinations thereof.

The group

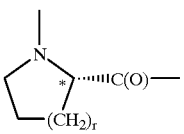

wherein r is 0, 1, or 2 is referred to as azetidine-2-carbonyl, prolinyl, or homoprolinyl, and is abbreviated Azt, Pro or hPro, respectively.

The group

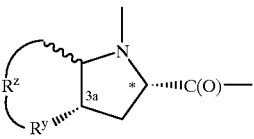

represents a saturated bicyclic system of the 4,5; 5,5; 6,5; 7,5; or 8,5 type. The stereochemistry at 3a is cis to the carbonyl; the other bridgehead bond may be either cis or trans except that the 4,5 and 5,5 systems must be cis at the bridgehead. The definitions of R$^y$ and R$^z$ provide that the variable ring, which includes the three carbon atoms shown, is a saturated carbocyclic system of 4–8 atoms. All of the ring atoms may be carbon, or one of the ring atoms may be a hetero atom selected from —O—, —S—, and —NH—. This definition includes the moiety derived from octahydroindole-2-carboxylic acid, as represented by

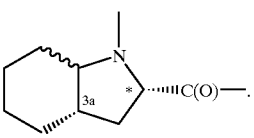

The various cis and trans forms of this moiety are contemplated by this invention. The preferred isomer derived from [2S-(2α,3aβ,7aβ)]-octahydro-indole-2-carboxylic acid is abbreviated "Ohi" and is represented by

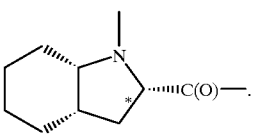

The asterisks in radical Y denote a chiral center that corresponds to (L) in the natural amino acids. The asterisk in radical X denotes a chiral center that is (D) or (DL); the # in radical X denotes a chiral center that is (L).

It will be appreciated that certain compounds of Formula I may exist in, and be isolated in, isomeric forms, including tautomeric forms or cis- or trans-isomers, as well as optically active racemic or diastereomeric forms. The present invention encompasses a compound of Formula I in any of the tautomeric forms or as a mixture thereof. It is to be understood that the present invention encompasses a compound of Formula I as a mixture of diastereomers, as well as in the form of an individual diastereomer, and that the present invention encompasses a compound of Formula I as a mixture of enantiomers, as well as in the form of an individual enantiomer, any of which mixtures or form possesses inhibitory properties against thrombin, it being well known in the art how to prepare or isolate particular forms and how to determine inhibitory properties against thrombin by standard tests including those described below.

In addition, a compound of Formula I may exhibit polymorphism or may form a solvate with water or an organic solvent. The present invention also encompasses any such polymorphic form, any solvate or any mixture thereof.

Particular values are listed below for radicals (either alone or as part of another radical), substituents, and ranges, for illustration only, and they do not exclude other defined values or other values within defined ranges for the radicals and substituents.

A particular value for a $(C_1-C_4)$alkyl group, a $(C_1-C_6)$ alkyl group, a $(C_1-C_8)$alkyl group or a $(C_1-C_{10})$alkyl group is methyl, ethyl, propyl, isopropyl, butyl, isobutyl or t-butyl. A particular value for a $(C_1-C_4)$alkoxy group is methoxy, ethoxy, propoxy, isopropoxy, or t-butyloxy. A particular value for a $(C_3-C_8)$cycloalkyl group is cyclopropyl, cyclopentyl or cyclohexyl. A particular value for a $(C_1-C_4)$ fluoroalkyl group is trifluoromethyl or 2,2,2-trifluoroethyl. A particular value for aryl is phenyl, naphthyl, furyl, thienyl, pyridyl, indolyl, quinolinyl or isoquinolinyl.

A particular compound of Formula I as defined above is one in which

X—C(O)— is D-homoprolinyl,

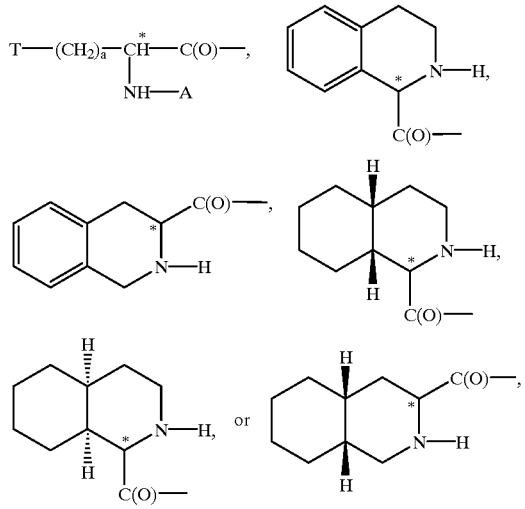

in which T is cyclohexyl or phenyl; a is 0 or 1; and A is hydrogen, $(C_1-C_4)$alkyl, $(C_1-C_4$ alkyl)sulfonyl, $(C_1-C_4$ alkyl)-oxy-carbonyl, $(C_1-C_4$ alkyl)carbonyl or carboxymethyl; and —Y—G— is —NR$^g$—CH$_2$—G—,

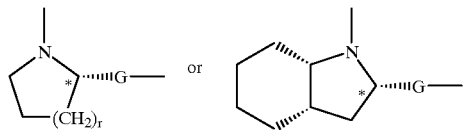

in which R$^g$ is $(C_1-C_6)$alkyl, —(CH$_2)_q$—$(C_3-C_8)$cycloalkyl or —(CH$_2)_q$-phenyl; q is 0, 1, 2 or 3; and r is 0, 1, or 2;

or a pharmaceutically acceptable salt thereof.

A preferred compound of Formula I as defined above is one in which

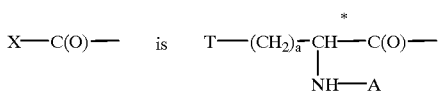

wherein T is cyclohexyl; a is 1; and A is hydrogen, ethylsulfonyl or carboxymethyl, particularly carboxymethyl; and —Y—G— is

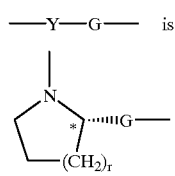

in which r is 0 or 1;

or a pharmaceutically acceptable salt thereof.

For any of the above defined compounds of Formula I, a particular value of —G—R is —C(O)—NH—(CH$_2)_s$—R; and a preferred value of —G—R is —C(O)—NH—(CH$_2)_s$—R in which s is 1, i.e. —C(O)—NH—CH$_2$—R.

A particular compound of Formula I in which —G—R is —C(O)—NH—CH$_2$—R and the other groups have any of the above definitions may be denoted by Formula Ia

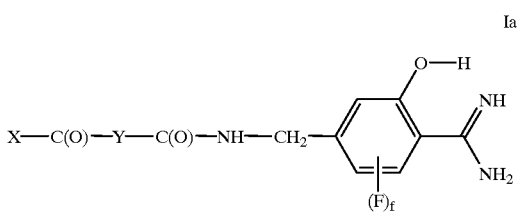

in which f is 0, 1, 2 or 3.

For any of the above defined compounds of Formula I, a particular value for R is 4-amidino-3-hydroxyphenyl or 4-amidino-3-hydroxy-2,5,6-trifluorophenyl; and a more particular value is 4-amidino-3-hydroxyphenyl.

A particular compound of the invention is one of those described herein as Example 1, 2, 3, 4, 5, 9, 10 or 11; and a preferred compound is one described as Example 1, 3 or 5, particularly Example 3; or a pharmaceutically acceptable salt thereof.

A compound of Formula I may be made by processes which include processes known in the chemical art for the production of structurally analogous compounds or by a novel process described herein. Novel processes and intermediates for the manufacture of a compound of Formula I as defined above provide further features of the invention and are illustrated by the following procedures in which the meanings of the generic radicals are as defined above, unless otherwise specified. It will be recognized that it may be preferred or necessary to prepare a compound of Formula I in which a functional group is protected using a conventional protecting group, then to remove the protecting group to provide the compound of Formula I.

(A) For a compound of Formula I in which —G—R is —C(O) —N—(CH$_2)_s$—R, coupling an acid of Formula II,

or an activated derivative thereof, with an amine of Formula III.

The coupling is carried out using a conventional procedure, for example by using a coupling reagent such as benzotriazol-1-yloxytripyrrolidinophosphonium hexafluorophosphate, for example as described in Example 1-E, or such as 1-(3-dimethylaminopropyl)-3-ethylcarbodiimide, for example as described in Example 5.

(B) Coupling an acid of Formula IV,

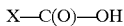            IV or an activated derivative thereof, with an amine of Formula V.

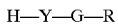            V

The coupling is carried out using a conventional procedure, such as by using one of the methods described above in (A).

(C) Hydrogenolyzing the N-O bond of a corresponding compound of Formula VI

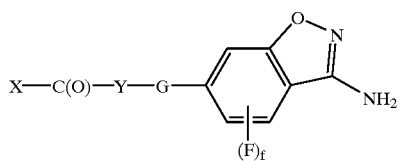            VI in which f is 0, 1, 2 or 3. Conveniently, the hydrogenolysis is carried out using a palladium on carbon catalyst in acidic, aqueous alchohol at ambient temperature and under hydrogen at ambient or a few bars' pressure; and the product is isolated as its acid addition salt.

Whereafter, for any of the above procedures, when a functional group is protected using a protecting group, removing the protecting group.

Whereafter, for any of the above procedures, when a pharmaceutically acceptable salt of a compound of Formula I is required, it is obtained by reacting the acidic or basic form of such a compound of Formula I with a base or an acid affording a physiologically acceptable counterion or by any other conventional procedure, such as, for example, exchanging the counterion of a salt.

A compound corresponding to compound of Formula I in which one or more functional groups is protected provides another aspect of the invention. Such a compound may be represented as a compound of Formula Ip

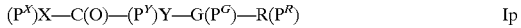            Ip which bears one or more of the protecting groups $P^X$, $P^Y$, $P^G$ and $P^R$ wherein $P^X$ is an optional protecting group(s) for a functional group(s) of X—C(O)—; $P^Y$ is an optional protecting group(s) for a functional group(s) of —Y—; $P^G$ is an optional amino protecting group for G when G-R is —(CH$_2$)—NH—(CH$_2$)$_s$—R; and $P^R$ is an optional protecting group(s) for a functional group of R. Typical values for $P^X$ and $P^Y$ include the groups which form a t-butylester or benzyl ester when the protected functional group is carboxy, the groups which form a t-butyl urethane or a benzyl urethane when the protected functional group is amino, and the groups which form a methyl ether, t-butyl ether or benzyl ether when the protected functional group is hydroxy. It will be recognized that some compounds of Formula I may serve as a protected equivalent of another compound of Formula I. For example, a compound of Formula I in which A is R"OC(O)— wherein R" is t-butyl is a protected equivalent of a compound of Formula I in which A is hydrogen, as described in Example 1. Similarly, a compound of Formula I in which $R^m$ is —COOR$^b$ wherein R$^b$ t-butyl is a protected equivalent of a compound of Formula I in which $R^m$ is —COOR$^b$ and R$^b$ is hydrogen.

As mentioned above, the invention includes a pharmaceutically acceptable salt of a thrombin inhibiting compound defined by the above Formula I. A particular benzamidine of this invention possesses one or more sufficiently basic functional groups to react with any of a number of nontoxic inorganic and organic acids to form a pharmaceutically acceptable salt. Acids commonly employed to form acid addition salts are inorganic acids such as hydrochloric acid, hydrobromic acid, hydroiodic acid, sulfuric acid, phosphoric acid, and the like, and organic acids such as p-toluene sulfonic, methanesulfonic acid, oxalic acid, p-bromo phenyl sulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of Formula I in which X or Y bears an acidic moiety, such a a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, the necessary starting materials for the preparation of a compound of Formula I may be prepared by procedures which are selected from standard techniques of organic chemistry, including aromatic and heteroaromatic substitution and transformation, from techniques which are analogous to the syntheses of known, structurally similar compounds, especially peptide syntheses, and techniques which are analogous to the above described procedures or procedures described in the Examples. It will be clear to one skilled in the art that a variety of sequences is available for the preparation of the starting materials. Starting materials and procedures which are novel provide further aspects of the invention.

A starting material acid of Formula II also may be represented as an acid of Formula IIp

            IIp in which $P^X$ and $P^Y$ are optional protecting groups as defined above. Conveniently, an acid of Formula IIp may be prepared by coupling an optionally protected acid of Formula VII

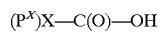            VII with an amino acid derivative of Formula VIII

  VIII in which $P^C$ is hydrogen or a carboxy protecting group, such as for example methyl, ethyl, t-butyl or benzyl, followed by removal of the protecting group $P^C$, when present.

A convenient general route for the preparation of an amine of Formula III or an amine of Formula V is outlined in Scheme I, in which $G^a$ represents a latent or protected form of the group $H_2N-(CH_2)_s-$ or the group $H-Y-G-$, respectively, and f is 0, 1, 2 or 3.

A starting material of Formula VI may be prepared by a route analogous to one described above, for example by using a compound of Formula XIV or Formula XV, or a protected derivative thereof.

A compound of the invention is isolated best in the form of an acid addition salt. A salt of the compound of Formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compound.

Scheme I

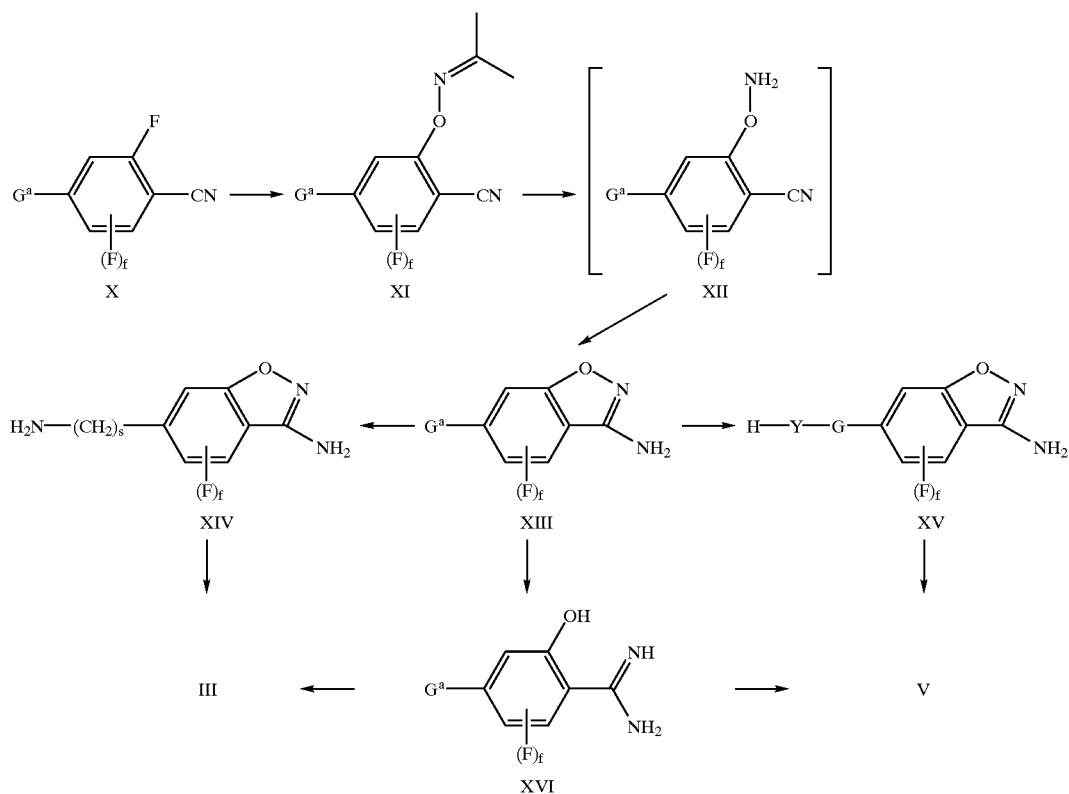

Thus, according to the method of Shutske and Kapples (*J. Heterocyclic Chem.* (1989), 26, 1293–1298), an ortho-fluoro benzonitrile of Formula X is treated with the potassium anion of acetone oxime to afford the corresponding oxime of Formula XI; acid hydrolysis of the oxime affords the amine of Formula XII which cyclizes in situ to afford the substituted 3-amino-1,2-benzisoxazole derivative of Formula XIII. The group $G^a$ may be converted into $H_2N-(CH_2)_s-$ to afford an amine of Formula XIV or into $H-Y-G$ to afford an amine of Formula XV, respectively; hydrogenolysis of the benzisoxazole, using a procedure similar to that described in (C) above, then affords the respective amine of Formula III or Formula V. Alternatively, it may be preferred to first hydrogenolyze the benzisoxazole of Formula XIII to a corresponding compound of Formula XVI before transforming the group $G^a$ to afford an amine of Formula III or Formula V. As described at Example 1-D and at Example 2-B, the conversion of $G^a$ (as cyano) into $H_2N-CH_2-$ may be performed at the same time as the hydrogenolysis, thus providing a "one-pot" conversion of a compound of Formula XIII into an amine of Formula III.

One of the novel intermediates of the invention is a compound of Formula III, or a salt and/or protected derivative thereof. A particular compound of Formula III is one in which s is 1 and which may be represented by Formula IIIa

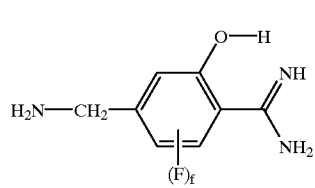  IIIa in which f is 0, 1, 2 or 3. A particular compound of Formula IIIa is one in which f is 0 or 3.

An additional aspect of the invention is the use of a compound of Formula III (or Formula IIIa) as defined above, or a salt or protected derivative thereof, as a starting material in the synthesis of a thrombin inhibitor.

As another aspect of the invention, there is provided a novel structural fragment of the formula

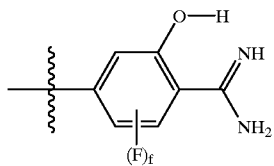

wherein f is 0, 1, 2 or 3 (particularly f is 0 or 3) as a novel structural element in a thrombin inhibitor, particularly in a peptidomimetic thrombin inhibitor.

Another novel intermediate of the invention is a compound of Formula XIII in which $G^a$ is cyano and which may be represented by Formula XIIIa

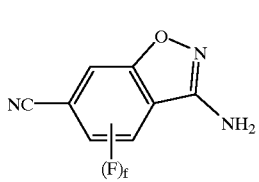

XIIIa wherein f is 0, 1, 2 or 3; particularly wherein f is 0 or 3.

As noted above, the optically active isomers and diastereomers of the compounds of Formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit thrombin over other proteinases and nonenzyme proteins involved in blood coagulation without appreciable interference with the body's natural clot lysing ability (the compounds have a low inhibitory effect on fibrinolysis). Also, they generally exhibit increased selectivity for thrombin compound to the prior amidinophenyl compounds. Further, such selectivity is believed to permit use with thrombolytic agents without substantial interference with thrombolysis and fibrinolysis.

The invention in one of its aspects provides a method of inhibiting thrombin in mammals comprising administering to a mammal in need of treatment an effective (thrombin inhibiting) dose of a compound of Formula I.

In another of its aspects, the invention provides a method of treating a thromboembolic disorder comprising administering to a mammal in need of treatment an effective (thromboembolic disorder therapeutic and/or prophylactic amount) dose of a compound of Formula I.

The invention in another of its aspects provides a method of inhibiting coagulation in a mammal comprising administering to a mammal in need of treatment an effective (coagulation inhibiting) dose of a compound of Formula I.

The thrombin inhibition, coagulation inhibition and thromboembolic disorder treatment contemplated by the present method includes both medical therapeutic and/or prophylactic treatment as appropriate.

In a further embodiment the invention relates to treatment, in a human or other mammal, of conditions where inhibition of thrombin is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally, parenterally e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides pharmaceutical compositions for use in the above described therapeutic method. Pharmaceutical compositions of the invention comprise an effective thrombin inhibiting amount of a compound of formula I in association with a pharmaceutically acceptable carrier, excipient or diluent. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 ml sterile glass ampoule. Another example of a unit dosage formulation comprises about 10 mg of a compound of the present invention as a pharmaceutically acceptable salt in 20 ml of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration. Another embodiment of the present invention is a pharmaceutical composition comprising an effective amount of a compound of Formula I or a pharmaceutically acceptable salt or solvate thereof in association with a pharmaceutically acceptable carrier, diluent or excipient therefor.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to Formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| Active ingredient | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly.

The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| Active ingredient | 100 mg |
|---|---|
| Isotonic saline | 1,000 ml |

The solution of the above ingredients generally is administered intravenously to a subject at a rate of 1 ml per minute.

The ability of a compound of the present invention to be an effective and orally active thrombin inhibitor is evaluated in one or more of the following assays.

The compounds provided by the invention (Formula I) selectively inhibit the action of thrombin in mammals. The inhibition of thrombin is demonstrated by in vitro inhibition of the amidase activity of thrombin as measured in an assay in which thrombin hydrolyzes the chromogenic substrate, N-benzoyl-L-phenylalanyl-L-valyl-L-arginyl-p-nitroanilide, N-benzoyl-L-Phe-L-Val-L-Arg-p-nitroanilide.

The assay is carried out by mixing 50 $\mu$l buffer (0.03M Tris, 0.15M NaCl, pH 7.4) with 25 $\mu$l of human thrombin solution (purified human thrombin, Enzyme Research Laboratories, South Bend, Ind., at 8 NIH units/ml) and 25 $\mu$l of test compound in a solvent (50% aqueous methanol (v:v)). Then 150 $\mu$l of an aqueous solution of the chromogenic substate (at 0.25 mg/ml) are added and the rates of hydrolysis of the substrate are measured by monitoring the reactions at 405 nm for the release of p-nitroaniline. Standard curves are constructed by plotting free thrombin concentration against hydrolysis rate. The hydrolysis rates observed with test compounds are then converted to "free thrombin" values in the respective assays by use of the standard curves. The bound thrombin (bound to test compound) is calculated by subtracting the amount of free thrombin observed in each assay from the known initial amount of thrombin used in the assay. The amount of free inhibitor in each assay is calculated by subtracting the number of moles of bound thrombin from the number of moles of added inhibitor (test compound).

The Kass value is the hypothetical equilibrium constant for the reaction between thrombin and the test compound (I).

$$\text{Thrombin} + I \rightleftarrows \text{Thrombin-I}$$

$$Kass = \frac{[\text{Thrombin-I}]}{[(\text{Thrombin}) \times (I)]}$$

Kass is calculated for a range of concentrations of test compounds and the mean value reported in units of liter per mole. In general, a thrombin inhibiting compound of Formula I of the instant invention exhibits a Kass of $0.1 \times 10^6$ L/mole or much greater. For example, each of the particularly preferred examples of the invention listed above was determined to have a Kass of at least $100 \times 10^6$ L/mole. Thus, the compounds of Examples 1, 3 and 5 were found to have a Kass of $770 \times 10^6$ L/mole, $1,200 \times 10^6$ L/mole and $100 \times 10^6$ L/mole, respectively.

By substantially following the procedures described above for human thrombin, and using other human blood coagulation system serine proteases and using fibrinolytic system serine proteases, with the appropriate chromogenic substrates, identified below, the selectivity of the compounds of the present invention with respect to the coagulation factor serine proteases and to the fibronolytic serine proteases are evaluated as well as their substantial lack of interference with human plasma clot fibrinolysis.

Human factors X, Xa, IXa, XIa, and XIIa are purchased from Enzyme Research Laboratories, South Bend, Ind.; human urokinase from Leo Pharmaceuticals, Denmark; and recombinant activated Protein C (aPC) is prepared at Eli Lilly and Co. substantially according to U.S. Pat. No. 4,981,952. Chromogenic substrates: N-Benzoyl-Ile-Glu-Gly-Arg-p-nitroanilide (for factor Xa); N-Cbz-D-Arg-Gly-Arg-p-nitroanilide (for factor IXa assay as the factor Xa substrate); Pyroglutamyl-Pro-Arg-p-nitroanilide (for Factor XIa and for aPC); H-D-Pro-Phe-Arg-p-nitroanilide (for factor XIIa); and Pyroglutamyl-Gly-Arg-p-nitroanilide (for urokinase); are purchased from Kabi Vitrum, Stockholm, Sweden, or from Midwest Biotech, Fishers, Ind. Bovine trypsin is purchased from Worthington Biochemicals, Freehold, N.J., and human plasma kallikrein from Kabi Vitrum, Stockholm, Sweden. Chromogenic substrate H-D-Pro-Phe-Arg-p-nitroanilide for plasma kallikrein is purchased from Kabi Vitrum, Stockholm, Sweden. N-Benzoyl-Phe-Val-Arg-p-nitroanilide, the substrate for human thrombin and for trypsin, is synthesized according to procedures described above for the compounds of the present invention, using known methods of peptide coupling from commercially available reactants, or purchased from Midwest Biotech, Fishers, Ind.

Human plasmin is purchased from Boehringer Mannheim, Indianapolis, Ind.: nt-PA is purchased as single chain activity reference from American Diagnostica, Greenwich, Conn.; modified-t-PA6 (mt-PA6) is prepared at Eli Lilly and Company by procedure known in the art (See, Burck, et al., *J. Biol. Chem.*, 265, 5120–5177 (1990). Plasmin chromogenic substrate H-D-Val-Leu-Lys-p-nitroanilide and tissue plasminogen activator (t-PA) substrate H-D-Ile-Pro-Arg-p-nitroanilide are purchased from Kabi Vitrum, Stockholm, Sweden.

In the chromogenic substrates described above the three-letter symbols Ile, Glu, Gly, Pro, Arg, Phe, Val, Leu and Lys are used to indicate the corresponding amino acid group isoleucine, glutamic acid, glycine, proline, arginine, phenylalanine, valine, leucine and lysine, respectively.

Thrombin inhibitors preferably should spare fibrinolysis induced by urokinase, tissue plasminogen activator (t-PA) and steptokinase. This would be important to the therapeutic use of such agents as an adjunct to streptokinase, t-PA or urokinase thrombolytic therapy and to the use of such agents as an endogenous fibrinolysis-sparing (with respect to t-PA and urokinase) antithrombotic agents. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Hazelton-LRE, Kalamazoo, Mich., U.S.A.) by venipuncture into 3.8 percent citrate. Fibrinogen is prepared from fresh dog plasma and human fibrinogen is prepared from in-date ACD human blood at the fraction I-2 according to previous procedures and specifications. Smith, *Biochem. J.*, 185, 1–11 (1980); and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased form Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 μl thrombin (73 NIH unit/ml) to 100 μl human plasma which contains 0.0229 μCi 125-iodine labeled fibrinogen. Clot lysis is studied by overlaying the clots with 50 μl of urokinase or streptokinase (50, 100, or 1000 unit/ml) and incubating for 20 hours at room temperature. After incubation the tubes are centrifuged in a Beckman Microfuge. 25 ul of supernate is added into 1.0 ml volume of 0.03M tris/0.15M NaCl buffer for gamma counting. Counting controls 100 percent lysis are obtained by omitting thrombin (and substituting buffer). The thrombin inhibitors are evaluated for possible interference with fibrinolysis by including the compounds in the overlay solutions at 1, 5, and 10 ug/ml concentrations. Rough approximations of $IC_{50}$ values are estimated by linear extrapolations from data points to a value which would represent 50 percent of lysis for that particular concentration of fibrinolytic agent.

Anticoaculant Activity

Materials

Dog plasma and rat plasma are obtained from conscious mixed-breed hounds (either sex, hazelton-LRE, Kalamazoo, Mich., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents ACTIN, Thromboplastin, and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The thrombin time (TT) is measured by adding 0.05 ml saline and 0.05 ml thrombin (10 NIH units/ml) to 0.05 ml test plasma. The activated partial thromboplastin time (APTT) is measured by incubation of 0.05 ml test plasma with 0.05 ml Actin reagent for 120 seconds followed by 0.05 ml $CaCl_2$ (0.02M). The prothrombin time (PT) is measured by adding 0.05 ml saline and 0.05 ml Thromboplastin-C reagent to 0.05 ml test plasma. The compounds of formula I are added to human or animal plasma over a wide range of concentrations to determine prolongation effects on the TT, APTT and PT assays. Linear extrapolations are performed to estimate the concentrations required to double the clotting time for each assay. Each of the particularly preferred examples of the invention listed above was determined to have a TT value of less than 50 ng/mL. For example, the respective values (in ng/mL) for TT were 6, 6 and 23 for the compounds of Examples 1, 3 and 5.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29,1982)

$FeCl_3$ model of arterial injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 ul is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269,1990).

Spontaneous thrombolysis model

In vitro data suggests that peptide thrombin inhibitors inhibit thrombin and at higher concentration may inhibit, other serine proteases, such as plasmin and tissue plasminogen activator. To assess if the compounds inhibit fibrinolysis in vivo, the rate of spontaneous thrombolysis is determined by implanting a labeled whole blood clot into the pulmonary circulation. Rat blood (1 ml) is mixed rapidly with bovine thrombin (4 IU, Parke Davis) and $^{125}I$ human Fibrogen (5 $\mu Ci$, ICN), immediately drawn into silastic tubing and incubated at 37° C. for 1 hour. The aged thrombus is expelled from the tubing, cut into 1 cm segments, washed 3× in normal saline and each segment is counted in a gamma counter. A segment with known counts is aspirated into a catheter that is subsequently implanted into the jugular vein. The catheter tip is advanced to the vicinity of the right atrium and the clot is expelled to float into the pulmonary circulation. One hour after implant, the heart and lungs are harvested and counted separately. Thrombolysis is expressed as a percentage where:

$$\% \text{ Thrombolysis} = \frac{(\text{injected } cpm - \text{lung } cpm)}{\text{injected } cpm} \times 100$$

The fibrinolytic dissolution of the implanted clot occurs time-dependently (see J. P. Clozel, *Cardiovas. Pharmacol.*, 12:520, 1988).

Coagulation parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 ml) is mixed with saline (0.1 ml) and bovine thrombin (0.1 ml, 30 U/ml in TRIS buffer; Parke Davis) at 37° C. For APTT, plasma (0.1 ml) and APTT solution (0.1 ml, Organon Teknika) are incubated for 5 minutes (37° C.) and $CaCl_2$ (0.1 ml, 0.025M) is added to start coagulation. Assays are done in duplicate and averaged.

Index of Bioavailability

A measure of bioactivity, plasma thrombin time (TT), serves as a substitute for the assay of parent compound on the assumption that increments in TT resulted from thrombin inhibition by parent only. The time course of the effect of the thrombin inhibitor upon TT is determined after i.v bolus administration to anesthetized rats and after oral treatment of fasted conscious rats. Due to limitations of blood volume and the number of points required to determine the time course from time of treatment to the time when the response returns to pretreatment values, two populations of rats are used. Each sample population represents alternating sequential time points. The average TT over the time course is used to calculate area under the curve (AUC). The index of bioavailability is calculated by the formula shown below and is expressed as percent relative activity.

The area under the curve (AUC) of the plasma TT time course is determined and adjusted for the dose. This index of bioavailability is termed "% Relative Activity" and is calculated as $$\% \text{ Relative Activity} = \frac{AUC\ po}{AUC\ iv} \times \frac{Dose\ iv}{Dose\ po} \times 100$$

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 ml/kg for i.v., and 5 ml/kg for p.o. and infusion volume is 3 ml/hr.

Statistics

Results are expressed as means ±SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months –2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic model

Test compound is formulated immediately prior to dosing by dissolving in sterile 0.9 percent saline to a 5 mg/ml preparation. Dogs are given a single 2 mg/kg dose of test compound by oral gavage. Blood samples (4.5 ml) are taken from the cephalic vein at 0.25, 0.5, 0.75, 1,2,3,4 and 6 hours after dosing. Samples are collected in citrated Vacutainer tubes and kept on ice prior to reduction to plasma by centrifugation. Plasma samples are analyzed by HPLC-MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Hazelton-LRE, Kalamazoo, Mich., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for $\geq$30 minutes.

Hematology and template bleeding time determinations

Whole blood cell counts, hemoglobin, and hematocrit values are determined on a 40-$\mu$l sample of citrated (3.8 percent) blood (1 part citrate: 9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide$\times$2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean $\pm$SEM. All studies are conducted in accordance with the guiding principles of the American Physiological Society. Further details regarding the procedures are described in Jackson, et al., *J. Cardiovasc. Pharmacol.*, 21, 587–599 (1993).

Compared to the corresponding amidino-phenyl compounds, the compounds of the instant invention, in which a hydroxy group is juxtaposed ortho to the amidino group, possess physio-chemical properties which are much more favorable for oral absorption. The logD (D=octanol/water distribution coefficient) at pH 7.4 [logD(7.4)] observed for the compound of Example 5 [logD(7.4)=1.91] exhibits a more favorable value than that of the reference compound [logD(7.4)=–3.89], a change [$\Delta$logD(7.4)] of 5.80 log units. For the compound of Example 3 [logD(7.4)= 0.55], compared with the corresponding amidino phenyl compound, $\Delta$logD(7.4)=1.13 log units was observed.

The following Examples are provided to further describe the invention and are not to be construed as limitations thereof.

The abbreviations used in the examples have the following meanings.

Amino acids: Azt=azetidine-2-carboxylic acid, Phe=phenylalamine, hPro=homo-proline, Pro=proline, Cha=$\beta$-cyclohexylalanine, Ohi=[2S-(2$\alpha$,3a$\beta$,7a$\beta$)]-octahydro-indol-2-carboxylic acid, (1R,4aR,8aR)-1-Piq=(1R,4aR,8aR)-1-perhydro-isoquinolinecarboxylate, Sar=sarcosine (N-methyl-glycine).

Anal.=elemental analysis
Boc=t-butyloxycarbonyl
Bn=benzyl
BOP-Cl=bis(2-oxo-3-oxazolidinyl)phosphinic chloride
t-Bu=t-butyl
n-BuLi=butyllithium
Cbz=benzyloxycarbonyl
18-Crown-6=1,4,7,10,13,16-hexaoxacyclooctadecane
DIBAL=diisobutylaluminum hydride
DMF=dimethylformamide
DMSO=dimethylsulfoxide
Et=ethyl
EtOAc=ethyl acetate
$Et_2O$=diethyl ether
EtOH=ethanol
FAB-MS=fast atom bombardment mass spectrum
FD-MS=field desorption mass spectrum
HPLC=High Performance Liquid Chromatography
HRMS=high resolution mass spectrum
HOBT=1-hydroxybenzotriazole hydrate
i-PrOH=isopropanol
IR=Infrared Spectrum
Me=methyl
MeOH=methanol
NMR=Nuclear Magnetic Resonance
RPHPLC=Reversed Phase High Performance Liquid Chromatography
$SiO_2$ silica gel
TEA=triethylamine
TFA=trifluoroacetic acid
THF=tetrahydrofuran
TLC=thin layer chromatography
Ts=tosyl (p-toluenesulfonyl)

The following parameters for preparative RPHPLC were employed: Solvent A: 0.05% aqueous hydrochloric acid (1.5 mL concentrated hydrochloric acid in 3 L water); Solvent B: acetonitrile; Gradient: as defined in each Example; Column: Vydac $C_{18}$–5 cm$\times$25 cm; Flow rate: 10 mL/minute.

Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

EXAMPLE 1

Preparation of D-cyclohexylalanyl-N-[[4-(aminoiminomethyl)-3-hydroxyphenyl]methyl]-L-prolinamide dihydrochloride

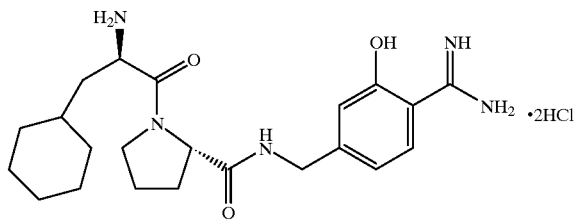

D-Cha-Pro-NHCH$_2$C$_6$H$_3$-3-OH-4-C(NH)NH$_2$•2HCl

A) Preparation of Boc-D-Cha-Pro-OH

A solution of Boc-D-Cha-OH (50.4 g, 185 mmol) in dichloromethane (360 mL) was cooled to 0° C. and N-hydroxysuccinimide (22.3 g, 194 mmol) was added. Then 1,3-dicyclohexylcarbodiimide (39.0 g, 189 mmol) was added in two portions as a solution in dichloromethane (90 mL). After stirring for 3 h at 0° C., L-Pro-OH (27.6 g, 240 mmol) and N,N-diisopropylethylamine (30.9 g, 239 mmol) were added. After stirring an additional 3 h between 0° C. and 10° C., the mixture was filtered over diatomaceous earth. The filter cake was rinsed with dichloromethane (100 mL); then the combined filtrates were concentrated in vacuo. The residual oil was partitioned between ethyl acetate (100 mL) and 0.625M aqueous NaHCO$_3$ (320 mL). The layers were separated, and the organic phase was washed with 0.625M aq. NaHCO$_3$ (80 mL). The combined bicarbonate extracts were then washed with ethyl acetate (100 mL). The aqueous phase was then stirred with ethyl acetate (300 mL) and acidified with 12N HCl (approximately 37 mL). The layers were separated and the acidic aqueous phase was extracted with ethyl acetate (100 mL). The combined ethyl acetate extracts were concentrated in vacuo. The residue was slurried with a minimal amount of ethyl acetate, filtered, washed again with ethyl acetate and dried to give 50.1 g (73%) of white powder.

$^1$H NMR
FAB-MS, m/e 369 (M$^+$)
Analysis for C$_{19}$H$_{32}$N$_2$O$_5$:
 Calc: C, 61.93; H, 8.75; N, 7.60;
 Found: C, 62.01; H, 8.96; N, 7.75.

B) Preparation of 2-fluoroterephthalonitrile

A solution of 4-bromo-2-fluorobenzonitrile (20 g, 100 mmol), zinc cyanide (7 g, 60 mmol) and tetrakis(triphenylphosphine)palladium (4.6 g, 4 mmol) in DMF (100 mL) was heated at 80° C. for 4 hr. Toluene (300 mL) and saturated aqueous ammonium chloride (300 mL) were added and the layers were separated. The organic layer was washed once with saturated aqueous ammonium chloride and twice with brine. The organic phase was dried (MgSO$_4$), filtered and concentrated. The product was purified by silica gel chromatography, eluting with a gradient of hexanes to 30% EtOAc/hexanes (11 g, 75%).

IR
$^1$H NMR
FD-MS, m/e 146 (M$^+$)
Analysis for C$_8$H$_3$FN$_2$:
 Calc: C, 65.76; H, 2.07; N, 19.17;
 Found: C, 65.69; H, 2.33; N, 19.05.

C) Preparation of 3-amino-1,2-benzisoxazole-5-carbonitrile

To a stirring solution of potassium t-butoxide (8.4 g, 75 mmol) in THF (100 mL) was added acetone oxime (5.5 g, 75 mmol). After stirring for 30 min, a solution of 2-fluoroterephthalonitrile (10 g, 68 mmol) in THF (50 mL) was added; and stirring was continued for an additional 2 hr. Saturated aqueous ammonium chloride (100 mL) was added and the solvents were removed in vacuo. The residue was partitioned between EtOAc and brine. The layers were separated and the organic phase was washed once with brine, dried (MgSO$_4$), filtered and concentrated. This crude solid was suspended in a solution of EtOH (150 mL), concentrated HCl (50 mL) and water (100 mL). This mixture was refluxed for 2 h. After cooling to room temperature, the solvents were removed in vacuo. The residue was treated with saturated aqueous sodium bicarbonate (200 mL), and the product was extracted by washing the aqueous layer three times with EtOAc. This organic solution was washed once with brine, dried (MgSO$_4$), filtered and concentrated to give a pink colored solid (9.4 g, 86%).

IR
$^1$H NMR
FD-MS, m/e 159 (M$^+$)
Analysis for C$_8$H$_5$N$_3$O:
 Calc: C, 60.38; H, 3.17; N, 26.40;
 Found: C, 60.96; H, 3.44; N, 25.58.

D) Preparation of 4-aminomethyl-2-hydroxybenzamidine dihydrochloride

3-Amino-1,2-benzisoxazole-5-carbonitrile (5 g, 31 mmol) was dissolved in EtOH (130 mL) 5% Pd/C (2.5 g) and 5N HCl (15 mL) were added and the mixture was hydrogenated at 4.1 bar on a shaker for 4 h. The catalyst was filtered, and the filtrate was concentrated to give a tan solid. This was titurated with diethyl ether and collected by filtration (3.2 g, 43%).

IR
$^1$H NMR
FD-NS, m/e 165 (M$^+$)
Analysis for C$_8$H$_{11}$N$_3$O•1HCl:
 Calc: C, 40.35; H, 5.50; N, 17.65; Cl, 29.78;
 Found: C, 40.75; H, 6.13; N, 15.91; Cl, 28.26.

E) Preparation of D-Cha-Pro-NHCH$_2$C$_6$H$_3$-3-OH-4-C(NH)NH$_2$•2HCl

To a stirring solution of Boc-D-Cha-Pro-OH (1.1 g, 2.9 mmol), 4-aminomethyl-2-hydroxybenzamidine dihydrochloride (0.71 g, 3 mmol) and diisopropylethylamine (1.7 mL, 10 mmol) in DMF (60 mL) was added benzotriazol-1-yloxy-tripyrrolidinophosphonium hexafluorophosphate (1.6 g, 3.1 mmol). After stirring overnight, the solvent was removed in vacuo. The resulting residue was partitioned between EtOAc and saturated aqueous ammonium chloride. The layers were separated and the organic phase was washed once with saturated aqueous ammonium chloride and twice with brine, dried (MgSO$_4$), filtered, and concentrated to give a residue. To this was added anisole (2.5 mL) and TFA (50 mL). The solution was stirred at room temp for 30 min, followed by removal of TFA in vacuo. The residue was dissolved in 1N HCl (50 mL) and washed twice with EtOAc. The crude product was concentrated in vacuo and purified by HPLC Method 1 using a gradient of 98/2 A/B to 50/50 A/B over 2.5 hr. Fractions containing only desired product (as judged by analytical HPLC) were pooled, concentrated and lyophilized to give a white powder (486 mg, 35%).

$^1$H NMR
FAB-MS, m/e 416.3 (MH$^+$)
Analysis for C$_{22}$H$_{33}$N$_5$O$_3$•2HCl:
 Calc: C, 54.10; H, 7.22; N, 14.34;
 Found: C, 53.89; H, 7.28; N, 14.07.

EXAMPLE 2

Preparation of D-cyclohexylalanyl-N-[[4-(aminoiminomethyl)-3-hydroxy-2,5,6-trifluorophenyl]methyl]-L-prolinamide dihydrochloride

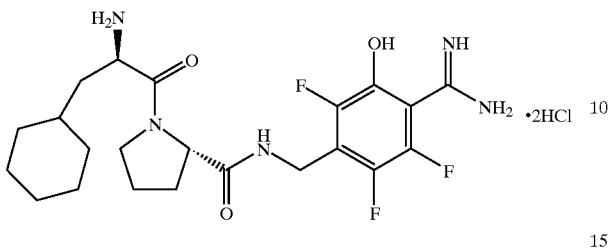

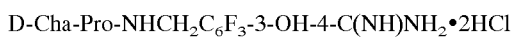

D-Cha-Pro-NHCH$_2$C$_6$F$_3$-3-OH-4-C(NH)NH$_2$•2HCl

A) Preparation of 3-amino-4,6,7-trifluoro-1,2-benzisoxazole-5-carbonitrile

To a stirring solution of N,N-diisopropylethylamine (19.2 g, 110 mmol) in CH$_3$CN (100 mL) was added acetone oxime (8 g, 110 mmol). After stirring for 30 min, a solution of tetrafluoroterephthalonitrile (20 g, 100 mmol) in CH$_3$CN (50 mL) was added; and the mixture was stirred overnight. Saturated aqueous ammonium chloride (100 mL) was added and the solvents were removed in vacuo. The residue was partitioned between EtOAc and brine. The layers were separated and the organic phase was washed once with brine, dried (MgSO$_4$), filtered and concentrated. This crude solid was suspended in EtOH (150 mL) and concentrated HCl (50 mL) and water (100 mL) were added. This was refluxed for 3 h. After cooling to room temperature, the solvents were removed in vacuo. The residue was treated with saturated aqueous sodium bicarbonate (200 mL), and the product was extracted by washing the aqueous layer three times with EtOAc. This organic solution was washed once with brine, dried (MgSO$_4$), filtered and concentrated to give a yellow solid. The crude product was purified by silica gel chromatography, eluting with a gradient of hexanes to 40% EtOAc/hexanes (9.2 g, 43%).

IR
$^1$H NMR
FD-MS, m/e 213 (M$^+$)
Analysis for C$_8$H$_2$F$_3$N$_3$O:
  Calc: C, 45.09; H, 0.95; N, 19.72; F, 26.74;
  Found: C, 45.47; H, 1.12; N, 19.39; F, 27.68.

B) Preparation of 4-aminomethyl-2-hydroxy-3,5,6-trifluorobenzamidine dihydrochloride 3-Amino-4,6,7-trifluoro-1,2-benzisoxazole-5-carbonitrile (5 g, 31 mmol) was dissolved in EtOH (130 mL). 5% Pd/C (2.5 g) and 5N HCl (15 mL) were added and the mixture was hydrogenated at 4.1 bar on a shaker for 4 h. The catalyst was filtered, and the filtrate was concentrated to give a white foam (7.4 g, 100%).

IR
$^1$H NMR
FD-MS, m/e 219 (M$^+$)
Analysis for C$_8$H$_8$F$_3$N$_3$O•2HCl:
  Calc: C, 32.90; H, 3.45; N, 14.38; Cl, 24.28;
  Found: C, 32.80; H, 4.00; N, 12.75; Cl, 22.22.

C) Preparation of D-Cha-Pro-NHCH$_2$C$_6$F$_3$-3-OH-4-C(NH)NH$_2$•2HCl

By methods substantially equivalent to those described in Example 1-E, 0.04 g of D-Cha-Pro-NHCH$_2$C$_6$F$_3$-3-OH-4-C(NH)NH$_2$•2HCl was prepared from 4-aminomethyl-2-hydroxy-3,5,6-trifluorobenzamidine dihydrochloride.

$^1$H NMR
FD-MS, m/e 470 (MH$^+$)
Analysis for C$_{22}$H$_{30}$F$_3$N$_5$O$_3$•2HCl:
  Calc: C, 48.71; H, 5.95; N, 12.91;
  Found: C, 48.90; H, 6.03; N, 12.86.

EXAMPLE 3

Preparation of N-carboxymethyl-D-cyclohexylalanyl-N-[[4-(aminoiminomethyl)-3-hydroxyphenyl]methyl]-L-prolinamide hydrochloride

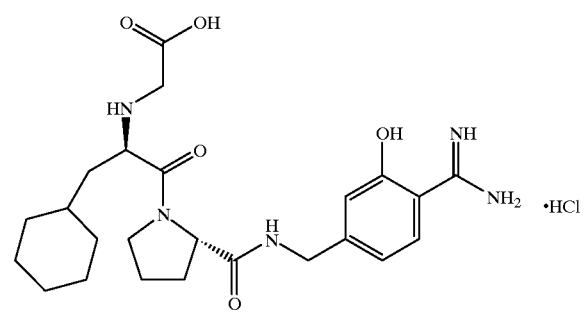

HO$_2$CCH$_2$-D-Cha-Pro-NHCH$_2$C$_6$H$_3$-3-OH-4-C(NH)NH$_2$•HCl

A) Preparation of N-(t-BuO$_2$CCH$_2$)-N-Boc-D-Cha-Pro-OH

To a solution of D-Phe-Pro-OBn•HCl (20 g, 51 mmol) in DMF (100 mL) was added t-butyl bromoacetate (9.9 g, 56 mmol) in one portion and N,N-diisopropylethylamine (17.4 mL, 101 mmol) dropwise over 30 min. This mixture was allowed to stir for 18 h. Di-t-butyl dicarbonate (16.6 g, 76 mmol) and N,N-diisopropylethylamine (13.2 mL, 76 mmol) were then added in one portion, and the reaction was allowed to stir an additional 24 h. The solvent was removed in vacuo and the residue was partitioned between EtOAc (1 L) and 1M aqueous citric acid (500 mL). The layers were separated and the organic phase was washed once with 1M aqueous citric acid, twice with saturated aqueous sodium bicarbonate, and once with brine (500 mL each). The organic phase was dried (Na$_2$SO$_4$), filtered, and concentrated in vacuo. The amber oil was purified by silica gel chromatography eluting with a EtOAc/hexanes gradient (hexanes to 30% EtOAc/hexanes). Fractions containing product were combined and concentrated to give 19.0 g (66%) of N-(t-BuOOCCH$_2$)-N-Boc-D-Phe-Pro-OBn as a colorless oil which slowly crystallized upon standing.

$^1$H NMR
FD-MS, m/e 566 (M$^+$)
Analysis for C$_{32}$H$_{42}$N$_2$O$_7$:
  Calc: C, 67.82; H, 7.47,; N, 4.94;
  Found: C, 68.06; H. 7.33; N, 5.17.

To a solution of N-(t-BuOOCCH$_2$)-N-Boc-D-Phe-Pro-OBn (18.5 g, 33 mmol) in EtOAc (250 mL) was added 5% Pd/C catalyst (5 g). This solution was degassed in vacuo several times and placed under an atmosphere of hydrogen for 2 h with stirring. The balloon was removed, diatomaceous earth was added and the slurry was filtered over a pad of diatomaceous earth. The filtrate was concentrated in vacuo to give 13.2 g (84%) of N-(t-BuO$_2$CCH$_2$)-N-Boc-D-Phe-Pro-OH as a white foam.

$^1$H NMR
FD-MS, m/e 476 (M$^+$)
Analysis for C$_{25}$H$_{36}$N$_2$O$_7$:
  Calc: C, 63.01; H, 7.61; N, 5.88;
  Found: C, 63.23; H, 7.73; N, 5.59.

N-(t-BuO$_2$CCH$_2$)-N-Boc-D-Phe-Pro-OH (13 g, 27 mmol) was dissolved in ethanol (750 mL) and PtO$_2$ (13 g) was added. The suspension was shaken under an atmosphere of hydrogen (4.1 bar) at 40° C. for 16 h. The catalyst was then filtered, and the filtrate was concentrated in vacuo to give 11.7 g (90%) of N-(t-BuO$_2$CCH$_2$)-N-Boc-D-Cha-Pro-OH as a white foam.

IR
$^1$H NMR
FD-MS, m/e 483 (M$^+$)
Analysis for C$_{25}$H$_{42}$N$_2$O$_7$:
  Calc: C, 62.22; H, 8.77; N, 5.80;
  Found: C, 62.99; H, 8.96; N, 5.48.

B) Preparation of HO$_2$CCH$_2$-D-Cha-Pro-NHCH$_2$C$_6$H$_3$-3-OH-4-C(NH)NH$_2$•HCl By methods substantially equivalent to those described in 1-E, 0.22 g of HO$_2$CCH$_2$-D-Cha-Pro-NHCH$_2$C$_6$H$_3$-3-OH-4-C(NH)NH$_2$•HCl was prepared.

$^1$H NMR
FD-MS, m/e 474.3 (MH$^+$)
Analysis for C$_{24}$H$_{35}$N$_5$O$_5$•1.5 HCl:
  Calc: C, 54.57; H, 6.96; N, 13.26;
  Found: C, 54.52; H, 6.95; N, 13.09.

EXAMPLE 4

Preparation of N-[[4-(aminoiminomethyl)-3-hydroxyphenyl]-methyl]-1-[(1R, 4aR,8aR)-perhydroisoquinolin-1-ylcarbonyl]-L-prolinamide dihydrochloride

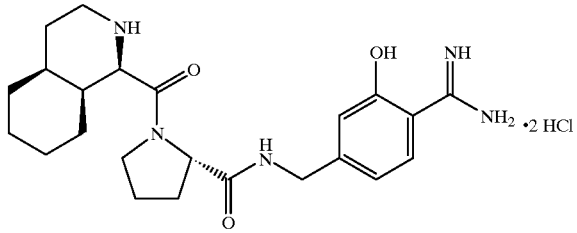

(1R, 4aR,8aR)-1-Piq-Pro-NHCH$_2$C$_6$H$_3$-3-OH-4-C(NH)NH$_2$•2HCl

1-[(1R,4aR,8aR)-2-Cbz-Perhydroisoquinolin-1-ylcarbonyl]-L-proline ([α]$_D$=−34.2° (C=0.5 MeOH)) was obtained as described in U.S. Pat. No. 5,430,023 at Example 25, column 23, line 23 through column 24, line 46. This compound also is known as Cbz-D-cis[4aR,8aR]-1-Piq-Pro-OH.

To a stirring solution of Cbz-(1R,4aR,8aR)-1-Piq-Pro-OH (1.1 g, 2.5 mmol), 4-aminomethyl-2-hydroxybenzamidine dihydrochloride (0.66 g, 2.75 mmol) and diisopropylethylamine (1.5 mL, 8.8 mmol) in DMF (60 mL) was added benzotriazol-1-yloxytripyrrolidinophosphonium hexafluorophosphate (1.4 g, 2.75 mmol). After stirring overnight, the solvent was removed in vacuo. The resulting residue was partitioned between EtOAc and saturated aqueous ammonium chloride. The layers were separated and the organic phase was washed once with saturated aqueous ammonium chloride and twice with brine, dried (MgSO$_4$), filtered, and concentrated to give a residue. This residue was dissolved in EtOH (100 mL) and water (50 mL). 1N HCl (5 mL) and 5% Pd/C (0.5 g) were added. The slurry was degassed and the mixture placed under a hydrogen atmosphere overnight. Diatomaceous earth was added and the slurry was filtered over a pad of diatomaceous earth and concentrated in vacuo. The crude product was purified by HPLC Method 1 using a gradient of 98/2 A/B to 30/70 A/B over 2.5 hr. Fractions containing pure product (as judged by analytical HPLC) were pooled, concentrated and lyophilized to give a white powder (0.22 g, 18%).

$^1$H NMR
FAB-MS, m/e 428.3 (MH$^+$)
Analysis for C$_{23}$H$_{33}$N$_5$O$_3$•2HCl:
  Calc: C, 55.20; H, 7.05; N. 13.99;
  Found: C, 54.93; H, 7.31; N, 14.00.

EXAMPLE 5

Preparation of N-ethylsulfonyl-D-cyclohexylalanyl-N-[[4-(aminoiminomethyl)-3-hydroxyphenyl]methyl]-L-prolinamide hydrochloride

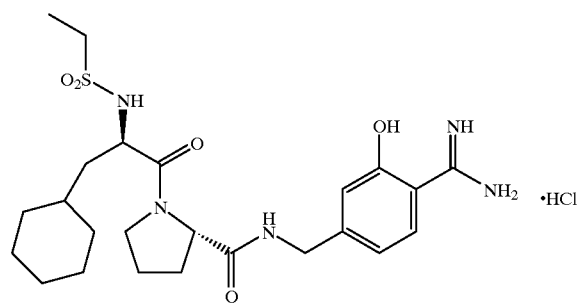

EtSO$_2$-D-Cha-Pro-NHCH$_2$C$_6$H$_3$-3-OH-4-C(NH)NH$_2$•HCl

A) Preparation of EtSO$_2$-D-Phe-OH

To a stirring suspension of D-phenylalanine (50 g, 300 mmol) in THF (400 mL) was added N,O-bis(trimethylsilyl)acetamide (92 g, 450 mmol). After stirring for 12 h, the solution was cooled to −78° C. and N,N-diisopropylethylamine (58 mL, 330 mmol) was added. To this solution was slowly added ethanesulfonyl chloride (31 mL, 330 mmol) and the cold bath was removed. After stirring for 20 h, the solvents were removed in vacuo and the residue was partitioned between saturated aqueous NaHCO$_3$ and ethyl acetate. The aqueous phase was washed with diethyl ether, acidified with solid citric acid and extracted twice with ethyl acetate. The combined ethyl acetate extracts were washed with brine, dried with MgSO$_4$, filtered and concentrated in vacuo to give 61 g (79%) of a thick colorless oil.

IR
$^1$H-NMR
FD-MS, m/e 257 (M$^+$)

B) Preparation of EtSO$_2$-D-Phe-Pro-OBn

To a stirring suspension of EtSO$_2$-D-Phe-OH (25.7 g, 100 mmol), Pro-OBn•HCl (26.6 g, 110 mmol), HOBT (13.5 g, 100 mmol) and N,N-diisopropylethylamine (43.5 mL, 250 mL) in THF (1 L) at 0° C. was added 1-(3-dimethylaminopropyl)-3-ethylcarbodiimide hydrochloride (23 g, 120 mL). After stirring for 20 h, the solvent was removed in vacuo and the residue was partitioned between ethyl acetate and 1N citric acid. The organic phase was washed twice with 1N KHCO$_3$, twice with brine, dried with MgSO$_4$, filtered and concentrated in vacuo. The residue was chromatographed over silica gel, eluting with a step gradient of hexanes through 50% ethyl acetate/hexanes. The product containing fractions were combined and concentrated in vacuo to give 29 g (65%) of a clear, thick oil.

IR
$^1$H-NMR
FD-MS, m/e 444 (M$^+$)

C) Preparation of EtSO₂-D-Phe-Pro-OH

To a solution of EtSO₂-D-Phe-Pro-OBn (28.5 g, 64 mmol) in ethyl acetate (500 mL) was added 10% Pd/C (5 g). The vessel was evacuated and placed under an atmosphere of hydrogen. After stirring for 16 h, the solution was filtered over diatomaceous earth, and the filter pad was then washed twice with methanol and filtered. The combined filtrates were concentrated in vacuo to give 22 g (97%) of off-white solid.

IR
¹H-NMR
FD-MS, m/e 355 (MH⁺)
Analysis for C₁₆H₂₂N₂O₅S:
  Calc: C, 54.22; H, 6.26; N, 7.90;
  Found: C, 53.98; H. 6.12; N, 7.63.

D) Preparation of EtSO₂-D-Cha-Pro-OH

To a solution of EtSO₂-D-Phe-Pro-OH (10 g, 28 mmol) in ethanol (300 mL) was added PtO₂ (5 g). The mixture was hydrogenated using a high pressure apparatus at 4.1 bar and 20° C. for 20 h. The solution was then filtered through diatomaceous earth, and concentrated to give 8.1 g (80%) of thick oil.

IR
¹H-NMR
FD-MS, m/e 361 (MH⁺)

E) Preparation of EtSO₂-D-Cha-Pro-NHCH₂C₆H₃-3-OH-4-C(NH) NH₂•2HCl

To a stirring solution of EtSO₂-D-Cha-Pro-OH (0.87 g, 2.4 mmol), 4-aminomethyl-2-hydroxybenzamidine dihydrochloride (0.63 g, 2.64 mmol) and diisopropylethylamine (1.5 mL, 8.8 mmol) in DMF (60 mL) was added benzotriazol-1-yloxytripyrrolidinophosphonium hexafluorophosphate (1.4 g, 2.75 mmol). After stirring overnight, the solvent was removed in vacuo. The residue was partitioned between 1N HCl and Et₂O. The layers were separated and the aqueous phase was washed three times with Et₂O and concentrated in vacuo. The crude product was purified by HPLC Method 1 using a gradient of 90/10 A/B to 40/60 A/B over 2.5 hr. Fractions containing pure product (as judged by analytical HPLC) were pooled, concentrated and lyophilized to give a white powder (0.30 g, 21%).

¹H NMR
FD-MS, m/e 508 (MH⁺)
Analysis for C₂₄H₃₇N₅O₅S•3HCl:
  Calc: C, 46.72; H, 6.53; N, 11.35;
  Found: C, 46.36; H, 6.16; N. 11.22.

EXAMPLE 6

Preparation of N-ethylsulfonyl-D-cyclohexylalanyl-N-[[4-(aminoiminomethyl)-3-hydroxy-2,5,6-trifluorophenyl]methyl]-L-prolinamide hydrochloride

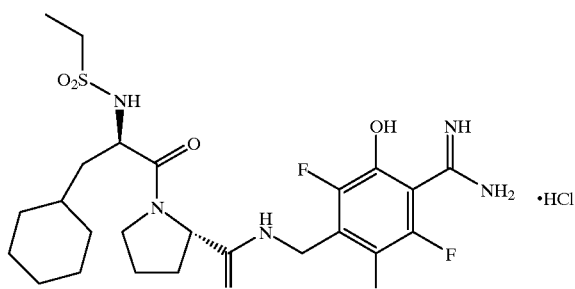

EtSO₂-D-Cha-Pro-NHCH₂C₆F₃-3-OH-4-C(NH)NH₂•HCl

By a method substantially equivalent to that described in Example 5, 0.54 g of EtSO₂-D-Cha-Pro-NHCH₂C₆F₃-3-OH-4-C(NH)NH₂•HCl was prepared starting from EtSO₂-D-Cha-Pro-OH and 4-aminomethyl-2-hydroxy-3,5,6-trifluorobenzamidine dihydrochloride.

¹H NMR
FAB-MS, m/e 562.2 (MH⁺)
Analysis for C₂₃H₃₄F₃N₅O₅S•2HCl:
  Calc: C, 45.43; H, 5.72; N, 11.04;
  Found: C, 45.54; H, 5.61; N, 11.03.

EXAMPLE 7

Preparation of 1-[N-ethylsulfonyl-D-phenylalanyl]-N-[[4-(aminoiminomethyl)-3-hydroxyphenyl]methyl]-[2S-(2α,3aβ,7aβ)]-octahydroindole-2-carboxamide hydrochloride

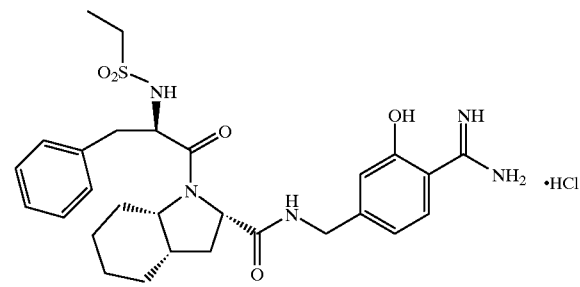

EtSO₂-D-Phe-Ohi-NHCH₂C₆H₃-3-OH-4-C (NH)NH₂•HCl

A) Preparation of [2S-(2α,3aβ,7aβ)]-octahydroindole-2-carboxylic acid ethyl ester•HCl (Ohi-OEt•HCl)

HCl gas was bubbled through a stirring suspension of (S)-indoline-2-carboxylic acid (20 g, 110 mmol) in ethanol (400 mL). When the acid was completely dissolved, the solution was brought to reflux. After 16 hours, the solution was cooled and the solvent removed in vacuo. The residue was triturated with diethyl ether and the resulting off-white solid was collected by filtration, washed with hexanes and dried overnight in a vacuum oven at 30° C. (25.5 g, 100%). This solid, (S)-indoline-2-carboxylic acid ethyl ester hydrochloride, was dissolved in ethanol (455 mL). To this was added 5% Pd/C (25.5 g) and the resulting suspension was hydrogenated at 4.1 bar on a shaker for 8 hours. The solution was filtered to remove catalyst and the filtrate was concentrated in vacuo. The residue was triturated with diethyl ether and the resulting solid was isolated by filtration to give 18.8 g (73%) of a white powder.

¹H NMR
FD-MS, m/e 197 (M⁺)
Analysis for C₁₁H₁₉NO₂•HCl:
  Calc: C, 56.53; H, 8.63; N, 5.99;
  Found: C, 56.24; H, 8.44; N, 6.00.

B) EtSO₂-D-Phe-Ohi-OEt

By methods substantially equivalent to those described in example 5, EtSO₂-D-Phe-Ohi-OEt was prepared (57%) from EtSO₂-D-Phe-OH and HCl-Ohi-OEt.

IR
¹H NMR
FD-MS, m/e 436.1 (M⁺)
Analysis for C₂₂H₃₂N₂O₅S:
  Calc: C, 60.53; H, 7.39; N, 6.42;
  Found: C, 60.62; H, 7.31; N, 6.22.

C) EtSO₂-D-Phe-Ohi-OH

To a stirring solution of EtSO₂-D-Phe-Ohi-OEt (12 g, 27.5 mmol) in p-dioxane (300 mL) was added a solution of LiOH•H₂O (2.3 g, 55 mmol) in water (150 mL). After stirring for 16 h, the solvent was removed in vacuo and the residue was redissolved in water and washed twice with diethyl ether. The aqueous phase was acidified with 5N HCl and the precipitate was filtered, washed with water and dried in vacuo to give 10.1 g (90%) of a light yellow solid.
IR
¹H NMR
FD-MS, m/e 409.1 (M⁺)
Analysis for $C_{20}H_{28}N_2O_5S$:
  Calc: C, 58.80; H, 6.91; N, 6.86;
  Found: C, 58.57; H, 7.00; N, 6.63.

D) Preparation of $EtSO_2$-D-Phe-Ohi-$NHCH_2C_6H_3$-3-OH-4-C(NH)$NH_2$•HCl

By methods substantially equivalent those described in Example 5, 400 mg of $EtSO_2$-D-Phe-Ohi-$NHCH_2C_6H_3$-3OH-4-C(NH)$NH_2$•HCl was obtained. HPLC Method 1 (gradient of 80/20 A/B to 30/70 A/B over 2.5 hr) was used.
¹H NMR
FD-MS, m/e 556.1 (MH⁺)
Analysis for $C_{28}H_{37}N_5O_5S$•2HCl•1.3H₂O:
  Calc: C, 51.58; H, 6.43; N, 10.74;
  Found: C, 51.51; H, 6.22; N, 10.71.

EXAMPLE 8

Preparation of 1-[N-ethylsulfonyl-D-cyclohexylalanyl]-N-[[4-(aminoiminomethyl)-3-hydroxyphenyl]methyl]-[2S-(2α,3aβ,7aβ)]-octahydroindole-2-carboxamide hydrochloride

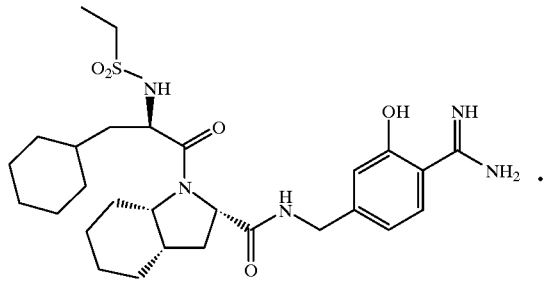

$EtSO_2$-D-Cha-Ohi-$NHCH_2C_6H_3$-3-OH-4-C (NH)$NH_2$•HCl

A) Preparation of $EtSO_2$-D-Cha-Ohi-OH

By methods substantially equivalent to those described in example 5-D, $EtSO_2$-D-Cha-Ohi-OH was prepared (95%) from $EtSO_2$-D-Phe-Ohi-OH.
IR
¹H-NMR
FD-MS, m/e 415.3 (MH⁺)

B) Preparation of $EtSO_2$-D-Cha-Ohi-$NHCH_2C_6H_3$-3-OH-4-C(NH)$NH_2$•HCl

By methods substantially equivalent to those described in Example 5-E, 744 mg was obtained.
¹H NMR
FD-MS, m/e 562.1 (MH⁺)
Analysis for $C_{28}H_{43}N_5O_5S$•2HCl•2H₂O:
  Calc: C, 50.15; H, 7.36; N, 10.44;
  Found: C, 50.31; H, 6.97; N, 10.49.

EXAMPLE 9

Preparation of 1-[N-ethylsulfonyl-D-phenylalanyl]-N-[[4-(aminoiminomethyl)-3-hydroxyphenyl]methyl]-S-azetidine-2-carboxamide hydrochloride

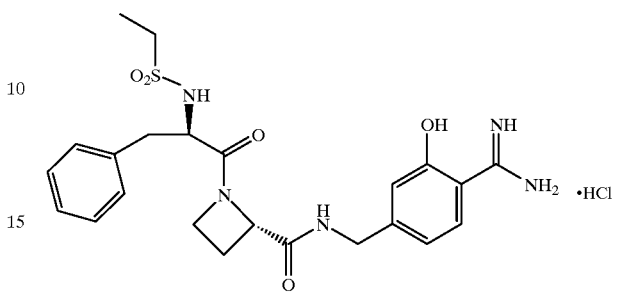

$EtSO_2$-D-Phe-Azt-$NHCH_2C_6H_3$-3-OH-4-C(NH)$NH_2$•HCl

By methods substantially equivalent to those described in Example 5, 350 mg was obtained.
¹H NMR
FD-MS, m/e 488.0 (MH⁺)
Analysis for $C_{23}H_{29}N_5O_5S$•3HCl:
  Calc: C, 46.28; H, 5.40; N, 11.73;
  Found: C, 46.22; H, 5.10; N, 11.49.

EXAMPLE 10

Preparation of 1-[N-ethylsulfonyl-D-cyclohexylalanyl]-N-[[4-(aminoiminomethyl)-3-hydroxyphenyl]methyl]-S-azetidine-2-carboxamide hydrochloride

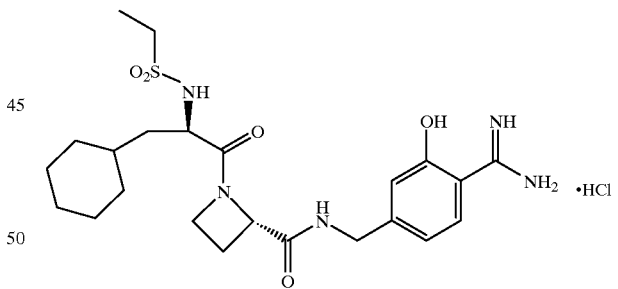

$EtSO_2$-D-Cha-Azt-$NHCH_2C_6H_3$-3-OH-4-C(NH)$NH_2$•HCl

By methods substantially equivalent to those described in Example 5, 284 mg was obtained.
¹H NMR
FD-MS, m/e 494.0 (MH⁺)
Analysis for $C_{23}H_{35}N_5O_5S$•2.5HCl•0.9H₂O:
  Calc: C, 45.97; H, 6.59; N, 11.65;
  Found: C, 46.25; H, 6.27; N, 11.31.

EXAMPLE 11

Preparation of N-ethylsulfonyl-D-phenylalanyl-N-[[4-(aminoiminomethyl)-3-hydroxyphenyl]methyl]-L-prolinamide hydrochloride

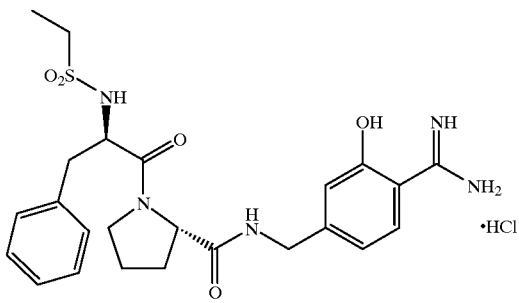

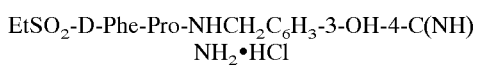

EtSO$_2$-D-Phe-Pro-NHCH$_2$C$_6$H$_3$-3-OH-4-C(NH)NH$_2$•HCl

By methods substantially equivalent to those described in Example 5, 151 mg was obtained.

$^1$H NMR

FD-MS, m/e 502.1 (MH$^+$)

Analysis for C$_{24}$H$_{31}$N$_5$O$_5$S•3HCl•1.5H$_2$O:

Calc: C, 45.18; H, 5.85; N, 10.97;

Found: C, 45.12; H, 5.45; N, 10.85.

EXAMPLE 12

Preparation of N-ethylsulfonyl-D-phenylalanyl-N-[[4-(aminoiminomethyl)-3-hydroxyphenyl]methyl]sarcosinamide hydrochloride

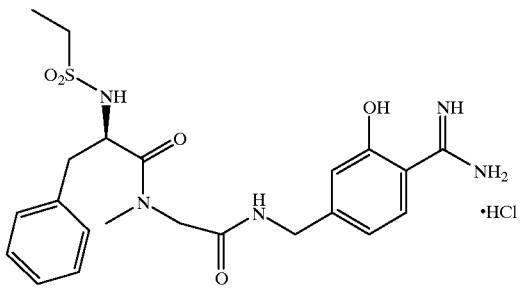

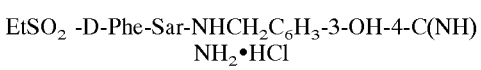

EtSO$_2$-D-Phe-Sar-NHCH$_2$C$_6$H$_3$-3-OH-4-C(NH)NH$_2$•HCl

By methods substantially equivalent to those described in Example 5, 151 mg was obtained.

$^1$H NMR

FD-MS, m/e 476.1 (MH$^+$)

Analysis for C$_{22}$H$_{29}$N$_5$O$_5$S•2.5HCl•0.5H$_2$O:

Calc: C, 45.90; H, 5.69; N, 12.16;

Found: C, 45.72; H, 5.36; N, 12.03.

What is claimed is:

1. An amine of Formula V

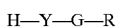

wherein —Y—G— is

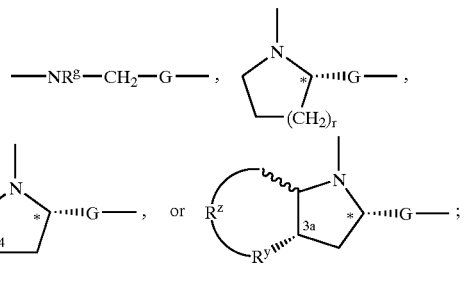

in which r is 0, 1 or 2;

R$^g$ is (C$_1$-C$_6$)alkyl, (C$_3$-C$_8$)cycloalkyl, or —(CH$_2$)$_p$—L—(CH$_2$)$_q$—T';

R$^p$ is (C$_1$-C$_6$)alkyl, (C$_3$-C$_8$)cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3; and T' is (C$_1$-C$_4$)alkyl, (C$_3$-C$_8$)cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or more heteroatoms which are the same or different and which are selected from sulfur, oxygen and nitrogen;

R$^y$ is —CH$_2$—, —O—, —S—, or —NH—; and

R$^z$ is a bond or, when taken with R$^y$ and the three adjoining carbon atoms, forms a saturated carbocyclic ring of 5–8 atoms, one atom of which may be —O—, —S—, or —NH—;

—G—R is —C(O)—NH—(CH$_2$)$_s$—R, —CH$_2$—NH—(CH$_2$)$_s$—R, —CH$_2$—NH—C(O)—R or —(CH$_2$)$_t$—O—R in which s is 1 or 2 and t is 1, 2 or 3; and R is a 4-amidino-3-hydroxyphenyl group bearing 0, 1, 2 or 3 fluoro substituents.

2. A compound of Formula VI

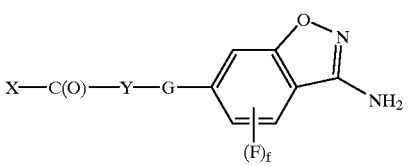

in which f is 0, 1, 2 or 3; and wherein

X—C(O)— is D-prolinyl, D-homoprolinyl, R$^m$—(CH$_2$)$_g$—NH—CH$_2$—C(O)—,

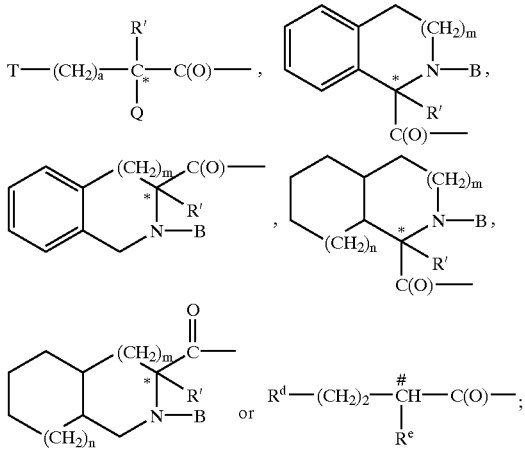

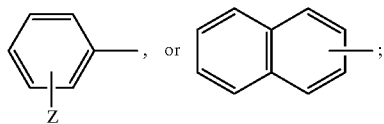

in which

R$^d$ is carboxy or methylsulfonyl;

R$^e$ is NHR$^c$, NHCOR$^c$ or NHCOOR$^c$; in which

R$^c$ is (C$_1$–C$_{10}$)alkyl, (C$_3$–C$_8$)cycloalkyl or a (C$_3$–C$_8$) cycloalkyl-(C$_1$–C$_6$)alkyl radical of 4–10 carbons;

T is (C$_3$–C$_8$)cycloalkyl, (C$_1$–C$_8$) alkyl,

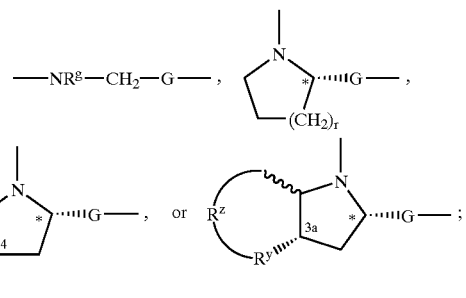

a is 0, 1 or 2; and

Q is —OH, (C$_1$–C$_4$)alkoxy, or —NH—A;

A is hydrogen, (C$_1$–C$_4$)alkyl, R"SO$_2$—, R"OC(O)—, R"C(O)—, R$^n$C(O)— or —(CH$_2$)$_g$—R$^m$;

g is 1, 2, or 3;

B is hydrogen or (C$_1$–C$_4$)alkyl;

R' is hydrogen or (C$_1$–C$_4$)alkyl;

R" is (C$_1$–C$_4$)alkyl, (C$_1$–C$_4$)fluoroalkyl bearing one to five fluoros, —(CH$_2$)$_d$—R$^m$, or unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R$^m$ is —COOR$^b$, —SO$_2$(C$_1$–C$_4$ alkyl), —SO$_3$H, —P(O)(OR$^b$)$_2$ or tetrazol-5-yl;

R$^n$ is —COOR$^b$ or tetrazol-5-yl;

each R$^b$ is independently hydrogen or (C$_1$–C$_4$)alkyl;

d is 1, 2, or 3;

m is 0, 1, or 2;

n is 0, 1, or 2; and

Z is hydrogen, (C$_1$–C$_4$)alkyl, (C$_1$–C$_4$)alkoxy, hydroxy, halo or (C$_1$–C$_4$)alkylsulfonylamino;

—Y—G— is

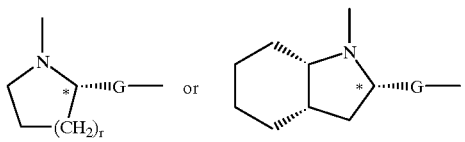

in which r is 0, 1 or 2;

R$^g$ is (C$_1$–C$_6$)alkyl, (C$_3$–C$_8$)cycloalkyl, or —(CH$_2$)$_p$—L—(CH$_2$)$_q$—T';

R$^p$ is (C$_1$–C$_6$)alkyl, (C$_3$–C$_8$)cycloalkyl, or —(CH$_2$)$_p$—L—(CH$_2$)$_q$—T';

where p is 0, 1, 2, 3, or 4; L is a bond, —O—, —S—, or —NH—; q is 0, 1, 2 or 3; and T' is (C$_1$–C$_4$)alkyl, (C$_3$–C$_8$)cycloalkyl, —COOH, —CONH$_2$, or Ar, where Ar is unsubstituted or substituted aryl, where aryl is phenyl, naphthyl, a 5- or 6-membered unsubstituted or substituted aromatic heterocyclic ring, having one or two heteroatoms which are the same or different and which are selected from sulfur, oxygen and nitrogen, or a 9- or 10-membered unsubstituted or substituted fused bicyclic aromatic heterocyclic group having one or two heteroatoms which are the same or different and which are selected from sulfur, oxygen and nitrogen;

R$^y$ is —CH$_2$—, —O—, —S—, or —NH—; and

R$^z$ is a bond or, when taken with R$^y$ and the three adjoining carbon atoms, forms a saturated carbocyclic ring of 5–8 atoms, one atom of which may be —O—, —S—, or —NH—; and —G— is —C(O)—NH—(CH$_2$)$_s$—, —CH$_2$—NH—(CH$_2$)$_s$—, —CH$_2$—NH—C(O)—or —(CH$_2$)$_t$—O— in which s is 1 or 2 and t is 1, 2 or 3.

3. The amine of claim 1 wherein halo is fluoro, chloro, bromo or iodo; a (C$_1$–C$_4$)alkyl group or a (C$_1$–C$_6$)alkyl group is methyl, ethyl, propyl, isopropyl, butyl, isobutyl or t-butyl; a (C$_1$–C$_4$)alkoxy group is methoxy, ethoxy, propoxy, isopropoxy, or t-butyloxy; a (C$_3$–C$_8$)cycloalkyl group is cyclopropyl, cyclopentyl or cyclohexyl; and aryl is phenyl, naphthyl, furyl, thienyl, pyridyl, indolyl, quinolinyl or isoquinolinyl.

4. The amine of claim 1 wherein —Y—G— is —NR$^g$—CH$_2$—G—, in which R$^g$ is (C$_1$–C$_6$)alkyl, —(CH$_2$)$_q$—(C$_3$–C$_8$)cycloalkyl or —(CH$_2$)$_q$-phenyl; q is 0, 1, 2 or 3; and r is 0, 1 or 2.

5. The amine of claim 4 wherein —Y—G— is

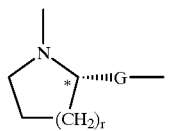

in which r is 0 or 1.

6. The amine of claim 3 wherein —G—R is —C(O)—NH—$(CH_2)_s$—R and s is 1.

7. The amine of claim 3 wherein —G—R is —C(O)—NH—$(CH_2)_s$—R and s is 1.

8. The amine of claim 4 wherein —G—R is —C(O)—NH—$(CH_2)_s$—R and s is 1.

9. The amine of any one of claims 1 and 4–7 wherein R is 4-amidino-3-hydroxyphenyl or 4-amidino-3-hydroxy-2,5,6-trifluorophenyl.

10. The amine of claim 9 wherein R is 4-amidino-3-hydroxyphenyl.

11. The compound of claim 2 wherein halo is fluoro, chloro, bromo or iodo; a $(C_1-C_4)$alkyl group, a $(C_1-C_6)$alkyl group, a $(C_1-C_8)$alkyl group or a $(C_1-C_{10})$alkyl group is methyl, ethyl, propyl, isopropyl, butyl, isobutyl or t-butyl; a $(C_1-C_4)$alkoxy group is methoxy, ethoxy, propoxy, isopropoxy, or t-butyloxy; a $(C_3-C_8)$cycloalkyl group is cyclopropyl, cyclopentyl or cyclohexyl; a $(C_1-C_4)$ fluoroalkyl group is trifluoromethyl or 2,2,2-trifluoroethyl; and aryl is phenyl, naphthyl, furyl, thienyl, pyridyl, indolyl, quinolinyl or isoquinolinyl.

12. The compound of claim 11 wherein X—C(O)— is D-homoprolinyl,

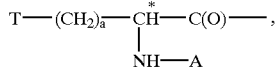

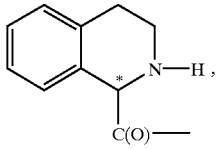

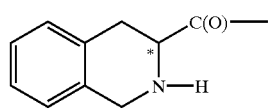

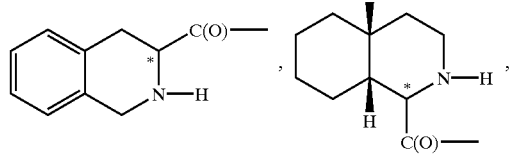

in which T is cyclohexyl or phenyl; a is 0 or 1; and A is hydrogen, $(C_1-C_4)$alkyl, $(C_1-C_4$ alkyl)sulfonyl, $(C_1-C_4$ alkyl)oxy-carbonyl, $(C_1-C_4$ alkyl)carbonyl or carboxymethyl; and —Y—G— is —$NR^g$—$CH_2$—G—,

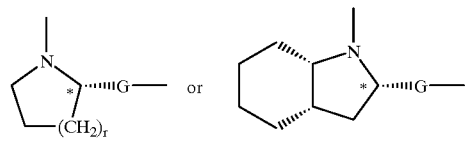

in which $R^g$ is $(C_1-C_6)$alkyl, —$(CH_2)_q$—$(C_3-C_8)$cycloalkyl or —$(CH_2)_q$-phenyl; q is 0, 1, 2 or 3; and r is 0, 1, or 2.

13. The compound of claim 12 wherein

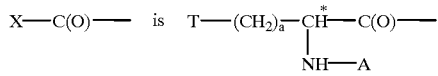

wherein T is cyclohexyl; a is 1; and A is hydrogen, ethylsulfonyl or carboxymethyl; and —Y—G— is

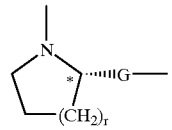

in which r is 0 or 1.

14. The compound of claim 13 wherein A is carboxymethyl.

15. The compound of any one of claims 2 and 11–14 wherein —G— is —C(O)—NH—$(CH_2)_s$— and s is 1.

16. The compound of claim 15 wherein f is 0 or 3.

17. The compound of claim 16 wherein f is 0.

* * * * *